(12) United States Patent
Testi et al.

(10) Patent No.: US 10,442,779 B2
(45) Date of Patent: Oct. 15, 2019

(54) COMPOSITIONS AND METHODS FOR TREATING FRIEDREICH'S ATAXIA

(71) Applicant: Fratagene Therapeutics S.R.L., Rome (IT)

(72) Inventors: Roberto Testi, Rome (IT); Ottaviano Incani, Rome (IT); Alessandra Rufini, Rome (IT); Gabriella DeMartino, Rome (IT)

(73) Assignee: FRATAGENE THERAPEUTICS S.R.L., Rome (IT)

( * ) Notice: Subject to any disclaimer, the term of this patent is extended or adjusted under 35 U.S.C. 154(b) by 209 days.

(21) Appl. No.: 14/862,072

(22) Filed: Sep. 22, 2015

(65) Prior Publication Data

US 2016/0083358 A1    Mar. 24, 2016

Related U.S. Application Data

(63) Continuation of application No. PCT/IB2015/057318, filed on Sep. 22, 2015.

(60) Provisional application No. 62/053,709, filed on Sep. 22, 2014.

(51) Int. Cl.
| | | |
|---|---|---|
| *C07D 279/20* | (2006.01) | |
| *A61K 31/5415* | (2006.01) | |
| *A61P 21/00* | (2006.01) | |

(52) U.S. Cl.
CPC .................. *C07D 279/20* (2013.01)

(58) Field of Classification Search
CPC .... A61K 31/5415; A61P 21/00; C07D 279/20
See application file for complete search history.

(56) References Cited

U.S. PATENT DOCUMENTS

| | | | |
|---|---|---|---|
| 8,703,749 B2 | 4/2014 | Testi et al. | |
| 8,815,230 B2 | 8/2014 | Testi et al. | |
| 2006/0025445 A1 | 2/2006 | Xiang et al. | |
| 2007/0197649 A1 | 8/2007 | Munnich et al. | |
| 2012/0149909 A1 | 6/2012 | Boliart et al. | |
| 2013/0109658 A1* | 5/2013 | Testi ..................... | A61K 31/63 514/155 |
| 2017/0296540 A1 | 10/2017 | Testi et al. | |

FOREIGN PATENT DOCUMENTS

| | | |
|---|---|---|
| EP | 1 378 753 A1 | 1/2002 |
| WO | 2006050819 A1 | 5/2006 |
| WO | 2012014083 A2 | 2/2012 |
| WO | 2012028961 A2 | 3/2012 |
| WO | 2012/149478 A2 | 11/2012 |
| WO | 2013/052613 A1 | 4/2013 |
| WO | 2016/046759 A2 | 3/2016 |
| WO | 2016/046759 A3 | 6/2016 |
| WO | 2016103223 A1 | 6/2016 |

OTHER PUBLICATIONS

Balcer et al. ("Consensus clinical management guidelines for Friedreich ataxia." FARA. Nov. 2014. http://www.curefa.org/pdf/research/ClinicalManagementGuidelinesForFA(1).pdf. 209 pages).*
Delatycki, M.B. ("Evaluating the progression of Friedreich ataxia and its treatment." JNeurol 256 Suppl 1, 36-41 (2009)).*
Mariotti et al. ("Erythropoietin in Friedreich ataxia." International Society for Neurochemistry, J. Neurochem. (2013) 126 (Suppl. 1), 80-87).*
J. G. Cannon Chapter Nineteen in Burger's Medicinal Chemistry and Drug Discovery, Fifth Edition, vol. I: Principles and Practice, Wiley-Interscience 1995, pp. 783-802.*
Patani et al. (Chemical Reviews, 1996, vol. 96, No. 8).*
Richardson et al. ("Development of potential iron chelators for the treatment of Friedreich's ataxia: ligands that mobilize mitochondrial iron." Biochimica et Biophysica Acta 1536 (2001) 133-140).*
Acquaviva, F., et al. Extra-mitochondrial localisation of frataxin and its association with IscU1 during enterocyte-like differentiation of the human colon adenocarcinoma cell line Caco-2. J Cell Sci 118, 3917-3924 (2005).
Adinolfi, S., et al. Bacterial frataxin Cya Y is the gatekeeper of iron-sulfur cluster formation catalyzed by IscS. Nat Struct Mal Biol 16, 390-396 (2009).
Al-Mahdawi, S., Pinto, R.M., Ismail, O., Varshney, D., Lymperi, S., Sandi, C., Trabzuni, D., and Pook, M. (2008). The Friedreich ataxia GAA repeat expansion mutation induces comparable epigenetic changes in human and transgenic mouse brain and heart tissues. Hum Mol Genet 17, 735-746.
Bedford, L., Lowe, J., Dick, L.R., Mayer, R.J., and Brownell, J.E., Ubiquitin-like protein conjugation and the ubiquitin-proteasome system as drug targets. Nature reviews Drug discovery 10, 29-46, (2011).
Berge et al., Pharmaceutical Salts; 1977, *J. Pharm. Sci.* 66:1-19.
Bidichandani, S.I., Ashizawa, T., and Patel, P.I. (1998). The GAA triplet-repeat expansion in Friedreich ataxia interferes with transcription and may be associated with an unusual DNA structure. Am J Hum Genet 62, 111-121.
Bocanegra-Garcia et al., Synthesis and Biological Evaluation of New Sulfonamide Derivatives as Potential Anti-Trypanosoma cruzi Agents; Medicinal Chemistry, 8(6), 1039-44; 2012.
Boström et al., Oxadiazoles in Medicinal Chemistry; J. Med. Chem. 2012, 55, 1817-30.
Boutet, S.C., Disatnik, M.H., Chan, L.S., Iori, K. & Rando, T.A. Regulation of Pax3 by proteasomal degradation of monoubiquitinated protein in skeletal muscle progenitors. Cell 130, 349-362 (2007).
Brady, G.P., Jr. & Stouten, P.F. Fast prediction and visualization of protein binding pockets with PASS. J Comput Aided Mol Des 14, 383-401 (2000).

(Continued)

*Primary Examiner* — Jeffrey S Lundgren
*Assistant Examiner* — Chris E Simmons
(74) *Attorney, Agent, or Firm* — Kilpatrick Townsend & Stockton LLP

(57) ABSTRACT

The invention provides compositions and methods useful for the treatment of Friedreich's ataxia. In some embodiments, the invention provides compositions and methods useful for inhibiting the ubiquitination of frataxin.

12 Claims, 9 Drawing Sheets

Specification includes a Sequence Listing.

(56) References Cited

OTHER PUBLICATIONS

Brownell, J.E., Sintchak, M.D., Gavin, J.M., Liao, H., Bruzzese, F.J., Bump, N.J., Soucy, T.A., Milhollen, M.A., Yang, X., Burkhardt, A.L., et al., Substrate-assisted inhibition of ubiquitin-like protein-activating enzymes: the NEDD8 E1 inhibitor MLN4924 forms a NEDD8-AMP mimetic in situ. Molecular cell 37, 102-111 (2010).
Bulteau, A.L., O'Neill, H.A., Kennedy, M.C., Ikeda-Saito, M., Isaya, G., and Szweda, L.I., Frataxin acts as an iron chaperone protein to modulate mitochondrial aconitase activity, Science 305, 242-245, (2004).
Campuzano, V., Montermini, L., Molto, M.D., Pianese, L., Cossee, M., Cavalcanti, F., Monros, E., Rodius, F., Duclos, F., Monticelli, A., et al. (1996). Friedreich's ataxia: autosomal recessive disease caused by an intronic GAA triplet repeat expansion. Science 271, 1423-1427.
Chatterjee et al., N-Methylation of Peptides and Proteins: An Important Element for Modulating Biological Functions; Angewandte Chemie 52 (1) (2013) 254-69.
Chen, Q., Xie, W., Kuhn, D.J., Voorhees, P.M., Lopez-Girona, A., Mendy, D., Corral, L.G., Krenitsky, V.P., Xu, W., Moutouh-de Parseval, L. et al., Targeting the p27 E3 ligase SCF(Skp2) results in p27- and Skp2-mediated cell-cycle arrest and activation of autophagy, Blood 111, 4690-4699 (2008).
Cnop, M., Mulder, H., and Igoillo-Esteve, M. (2013). Diabetes in Friedreich ataxia. J Neurochem 126 Suppl 1, 94-102.
Condò, I., Malisan, F., Guccini, I., Serio, D., Rufini, A., and Testi, R. (2010). Molecular control of the cytosolic aconitase/IRP1 switch by extramitochondrial frataxin. Hum Mol Genet 19, 1221-1229.
Condò, I., Ventura, N., Malisan, F., Rufini, A., Tomassini, B., and Testi, R., In vivo maturation of human frataxin. Hum Mol Genet 16, 1534-1540 (2007).
Condò, I., Ventura, N., Malisan, F., Tomassini, B., and Testi, R., A pool of extramitochondrial frataxin that promotes cell survival. J Biol Chem 281, 16750-16756 (2006).
Deshaies, R.J. & Joazeiro, C.A. RING domain E3 ubiquitin ligases. Annu Rev Biochem 78, 399-434 (2009).
Dhe-Paganon, S., Shigeta, R., Chi, Y.I., Ristow, M. & Shoelson, S.E., Crystal structure of human frataxin, J Biol Chem 275, 30753-30756 (2000).
Ding, K., Lu, Y., Nikolovska-Coleska, Z., Wang, G., Qiu, S., Shangary, S., Gao, W., Qin, D., Stuckey, J., Krajewski, K., et al., Structure-based design of spiro-oxindoles as potent, specific small-molecule inhibitors of the MDM2-p53 interaction. Journal of medicinal chemistry 49, 3432-3435 (2006).
Germain, D., Ubiquitin-dependent and -independent mitochondrial protein quality controls: implications in ageing and neurodegenerative diseases, *Mol Microbiol* 70, 1334-1341 (2008).
Ghorbani-Vaghei et al., Poly(N,N'-dichloro-N-ethylbenzene-1,3-disulfonamide) and N,N,N'N'-Tetra-chlorobenzene-1,3-disulfonamide as Novel Reagents for the Synthesis of N-Chloroamines, Nitriles and Aldehydes; Synthesis, (6), 945-50; 2009.
Glickman, M.H., and Ciechanover, A., The ubiquitin-proteasome proteolytic pathway: destruction for the sake of construction. Physiological reviews 82, 373-428 (2002).
Gottesfeld, J.M., Small molecules affecting transcription in Friedreich ataxia. Pharmacol Ther 116, 236-248 (2007).
Greene, E., Mahishi, L., Entezam, A., Kumari, D., and Usdin, K. (2007). Repeat-induced epigenetic changes in intron 1 of the frataxin gene and its consequences in Friedreich ataxia. Nucleic Acids Res 35, 3383-3390.
Habelhah, H. et al., Regulation of 2-oxoglutarate (alpha-ketoglutarate) dehydrogenase stability by the RING finger ubiquitin ligase Siah. *J Biol Chem* 279, 53782-53788 (2004).
He, Lingyan et al., Discovering Potent Inhibitors Against the β-Hydroxyacyl-Acyl Carrier Protein Dehydratase (FabZ) of Helicobacter pylori: Structure-Based Design, Synthesis, Bioassay, and Crystal Structure Determination; *J. Med. Chem.* 2009, 52(8), 2465-2481.

Herman, D., Jenssen, K., Burnett, R., Soragni, E., Perlman, S.L., and Gottesfeld, J.M., Histone deacetylase inhibitors reverse gene silencing in Friedreich's ataxia. Nat Chem Biol 2, 551-558 (2006).
Huang and Xu, Synthesis of imides and benzoylureas by direct oxidation of N-methylenes of amides and benzylureas; Journal of Chemical Research, 37(2), 77-79; 2013.
Irwin, J.J. & Shoichet, B.K., ZINC—a free database of commercially available compounds for virtual screening, *J Chem Inf Model* 45, 177-182 (2005).
Issaeva, N., Bozko, P., Enge, M., Protopopova, M., Verhoef, L.G., Masucci, M., Pramanik, A., and Selivanova, G., Small molecule RITA binds to p53, blocks p53-HDM-2 interaction and activates p53 function in tumors, Nature medicine 10, 1321-1328 (2004).
Iwai, K. & Tokunaga, F. Linear polyubiquitination: a new regulator of NF-kappaB activation. EMBO Rep 10, 706-713 (2009).
Kisselev, A.F., van der Linden, W.A., and Overkleeft, H.S., Proteasome inhibitors: an expanding army attacking a unique target, Chemistry & biology 19, 99-115, (2012).
Komander, D., The emerging complexity of protein ubiquitination. *Biochem Soc Trans* 37, 937-953 (2009).
Koutnikova, H., Campuzano, V., and Koenig, M. (1998). Maturation of wild-type and mutated frataxin by the mitochondrial processing peptidase. Hum Mol Genet 7, 1485-1489.
Kravtsova-Ivantsiv, Y., Cohen, S. & Ciechanover, A. Modification by single ubiquitin moieties rather than polyubiquitination is sufficient for proteasomal processing of the p105 NF-kappaB precursor. Mol Cell 33, 496-504 (2009).
Kussie, P.H., Gorina, S., Marechal, V., Elenbaas, B., Moreau, J., Levine, A.J., and Pavletich, N.P., Structure of the MDM2 oncoprotein bound to the p53 tumor suppressor transactivation domain, Science 274, 948-953 (1996).
Lakner et al., Synthesis of Novel Trisubstituted Imidazolines; Synthesis, (12), 1987-1990; 2009.
Lee et al., A practical synthesis of N-tosylimines of arylaldehydes; Tetrahedron Letters 44 (2003) 1231-34.
Li, W., et al. Genome-wide and functional annotation of human E3 ubiquitin ligases identifies MULAN, a mitochondrial E3 that regulates the organelle's dynamics and signaling. PLoS One 3, e1487 (2008).
Lim et al., "Protection against hydrogen peroxide-mediated cytotoxicity in Friedreich's ataxia fibroblasts using novel iron chelators of the 2-pyridylcarboxaldehyde isonicotinoyl hydrazone class", Molecular Pharmacology, vol. 74, No. 1, Apr. 24, 2008, pp. 225-235.
Luckhurst et al., A convenient synthesis of sulfonylureas from carboxylic acids and sulfonamides via an in situ Curtius rearrangement; Tetrahedron Letters 48 (2007) 8878-8882.
Marmolino, D. & Acquaviva, F., Friedreich's Ataxia: from the (GAA)n repeat mediated silencing to new promising molecules for therapy. Cerebellum 8, 245-259 (2009).
Marmolino, D., Acquaviva, F., Pinelli, M., Monticelli, A., Castaldo, I., Filla, A., and Cocozza, S., PPAR-gamma agonist Azelaoyl PAF increases frataxin protein and mRNA expression: new implications for the Friedreich's ataxia therapy, Cerebellum 8, 98-103 (2009).
Martelli, A., and Puccio, H., Dysregulation of cellular iron metabolism in Friedreich ataxia: from primary iron-sulfur cluster deficit to mitochondrial iron accumulation, Front Pharmacol 5, 130 (2014).
Musco, G., et al., Towards a structural understanding of Friedreich's ataxia: the solution structure of frataxin, *Structure* 8, 695-707 (2000).
Niwata et al., Substituted 3-(Phenylsulfonyl)-1-phenylimidazolidine-2, 4-dione Derivatives as Novel Nonpeptide Inhibitors of Human Heart Chymase; *J. Med. Chem.*, 1997, vol. 40, No. 14, 2156-63.
Pandolfo, M. & Pastore, A. The pathogenesis of Friedreich ataxia and the structure and function of frataxin. *J Neurol* 256 Suppl 1, 9-17 (2009).
Pandolfo, M., Friedreich ataxia: the clinical picture, J Neurol 256 Suppl 1, 3-8 (2009).
Parkinson, M.H., Boesch, S., Nachbauer, W., Mariotti, C., and Giunti, P., Clinical features of Friedreich's ataxia: classical and atypical phenotypes, J Neurochem 126 Suppl 1, 103-117 (2013).
Pastore, A., and Puccio, H. (2013). Frataxin: a protein in search for a function. J Neurochem 126 Suppl 1, 43-52.

(56) References Cited

OTHER PUBLICATIONS

Paupe, V., Dassa, E.P., Goncalves, S., Auchere, F., Lonn, M., Holmgren, A., and Rustin, P., Impaired nuclear Nrf2 translocation undermines the oxidative stress response in Friedreich ataxia, PLoS One 4, e4253 (2009).
PCT/IB2015/057318, "International Search Report and Written Opinion", dated Apr. 22, 2016, 25 pages.
PCT/IB2015/057318, "Invitation to Pay Additional Fees and Partial Search Report", dated Jan. 8, 2016, 10 pages.
PCT/IB2015/057318, "Written Opinion", dated Jun. 7, 2016, 15 pages.
Perdomini, M., Belbellaa, B., Monassier, L., Reutenauer, L., Messaddeq, N., Cartier, N., Crystal, R.G., Aubourg, P., and Puccio, H. (2014). Prevention and reversal of severe mitochondrial cardiomyopathy by gene therapy in a mouse model of Friedreich's ataxia. Nature medicine 20, 542-547.
Puccio, H., Multicellular models of Friedreich ataxia. *J Neurol* 256 Suppl 1, 18-24 (2009).
Rentsch, A., Landsberg, D., Brodmann, T., Bulow, L., Girbig, A.K., and Kalesse, M., Synthesis and pharmacology of proteasome inhibitors, Angewandte Chemie 52, 5450-5488 (2013).
Richardson et al., "Therapeutic strategies in Friedreich's Ataxia", Brain Res. Jun. 13, 2013; 1514: 91-97.
Richardson, P.G., Mitsiades, C., Hideshima, T., and Anderson, K.C., Bortezomib: proteasome inhibition as an effective anticancer therapy, Annu Rev Med 57, 33-47 (2006).
Rotig, A., de Lonlay, P., Chretien, D., Foury, F., Koenig, M., Sidi, D., Munnich, A., and Rustin, P., Aconitase and mitochondrial iron-sulphur protein deficiency in Friedreich ataxia, Nat Genet 17, 215-217 (1997).
Rotin, D. & Kumar, S. Physiological functions of the HECT family of ubiquitin ligases. Nat Rev Mol Cell Biol 10, 398-409 (2009).
Roxburgh, P., Hock, A.K., Dickens, M.P., Mezna, M., Fischer, P.M., and Vousden, K.H.Small molecules that bind the Mdm2 RING stabilize and activate p53, Carcinogenesis 33, 791-798.
Rufini et al., "Highly specific ubiquitin-competing molecules effectively promote frataxin accumulation and partially rescue the aconitase defect in Friedreich ataxia cells", Neurobiology of Disease., vol. 75, Mar. 1, 2015, pp. 91-99.
Rufini et al., "Preventing the ubiquitin-proteasome-dependent degradation of frataxin, the protein defective in Friedreich's ataxia", Human Molecular Genetics, Oxford University Press, GB, vol. 20, No. 7, Apr. 1, 2011, pp. 1253-1261.
Saeki, Y., et al. Lysine 63-linked polyubiquitin chain may serve as a targeting signal for the 26S proteasome. EMBO J 28, 359-371 (2009).
Sakamoto, N., Ohshima, K., Montermini, L., Pandolfo, M., and Wells, R.D. (2001). Sticky DNA, a self-associated complex formed at long GAA*TTC repeats in intron 1 of the frataxin gene, inhibits transcription. The Journal of biological chemistry 276, 27171-27177.
Schmucker, S., Argentini, M., Carelle-Calmels, N., Martelli, A. & Puccio, H. The in vivo mitochondrial two-step maturation of human frataxin. Hum Mal Genet 17, 3521-3531 (2008).
Schulz, J.B., Boesch, S., Burk, K., Durr, A., Giunti, P., Mariotti, C., Pousset, F., Schols, L., Vankan, P., and Pandolfo, M., Diagnosis and treatment of Friedreich ataxia: a European perspective. Nat Rev Neurol 5, 222-234 (2009).
Schulz, J.B., Di Prospero, N.A. & Fischbeck, K., Clinical experience with high-dose idebenone in Friedreich ataxia. J Neurol 256 Suppl 1, 42-45 (2009).
Schwartz, A.L. & Ciechanover, A., Targeting proteins for destruction by the ubiquitin system: implications for human pathobiology, Annu Rev Pharmacol Toxicol 49, 73-96 (2009).
Shan, Y., Schoenfeld, R.A., Hayashi, G., Napoli, E., Akiyama, T., Iodi Carstens, M., Carstens, E.E., Pook, M.A., and Cortopassi, G.A. (2013). Frataxin deficiency leads to defects in expression of antioxidants and Nrf2 expression in dorsal root ganglia of the Friedreich's ataxia YG8R mouse model. Antioxid Redox Signal 19, 1481-1493.

Shen, M., Schmitt, S., Buac, D., and Dou, Q.P., Targeting the ubiquitin-proteasome system for cancer therapy, Expert opinion on therapeutic targets 17, 1091-1108, (2013).
Soucy, T.A., Smith, P.G., Milhollen, M.A., Berger, A.J., Gavin, J.M., Adhikari, S., Brownell, J.E., Burke, K.E., Cardin, D.P., Critchley, S. et al., An inhibitor of NEDD8-activating enzyme as a new approach to treat cancer, Nature 458, 732-736 (2009).
Teague, S.J., Davis, A.M., Leeson, P.D. & Oprea, T. The Design of Leadlike Combinatorial Libraries. Angew Chem Int Ed Engl 38, 3743-3748 (1999).
Tomassini, B., Arcuri, G., Fortuni, S., Sandi, C., Ezzatizadeh, V., Casali, C., Condo, I., Malisan, F., Al-Mahdawi, S., Pook, M. et al., Interferon gamma upregulates frataxin and corrects the functional deficits in a Friedreich ataxia model, Hum Mol Genet 21, 2855-2861 (2012).
Treier, M., Staszewski, L.M. & Bohmann, D. Ubiquitin-dependent c-Jun degradation in vivo is mediated by the delta domain. Cell 78, 787-798 (1994).
Trott, O. & Olson, A.J. AutoDock Vina: improving the speed and accuracy of docking with a new scoring function, efficient optimization, and multithreading. J Comput Chem 31, 455-461 (2010).
Tsou, A.Y., Friedman, L.S., Wilson, R.B. & Lynch, D.R., Pharmacotherapy for Friedreich ataxia, CNS Drugs 23, 213-223 (2009).
Vanjari, et al., $MnO_2$ Promoted Sequential C—O and C—N Bond Formation via C—H Activation of Methylarenes: A New Approach to Amides; *Org. Lett.*, vol. 15, No. 18, 2013.
Vassilev, L.T., Vu, B.T., Graves, B., Carvajal, D., Podlaski, F., Filipovic, Z., Kong, N., Kammlott, U., Lukacs, C., Klein, C., et al., In vivo activation of the p53 pathway by small-molecule antagonists of MDM2, Science 303, 844-848 (2004).
Vaubel, R.A., and Isaya, G., Iron-sulfur cluster synthesis, iron homeostasis and oxidative stress in Friedreich ataxia, Mol Cell Neurosci 55, 50-61 (2013).
Wang et al., Silver catalyzed intramolecular cyclization for synthesis of 3-alkylideneoxindoles via C—H functionalization; Chemical Communications, 47(40), 11336-11338; 2011.
Wang et al., An expeditious and convenient synthesis of acylsulfonamides utilizing polymer-supported reagents; Tetrahedron Letters, 48(30), 5181-5184; 2007.
Weidemann, F., Stork, S., Liu, D., Hu, K., Herrmann, S., Ertl, G., and Niemann, M. (2013). Cardiomyopathy of Friedreich ataxia. J Neurochem 126 Suppl 1, 88-93.
Whitnall et al., "The MCK mouse heart model of Friedreich's ataxia: Alterations in iron-regulated proteins and cardiac hypertrophy are limited by iron chelation", Proceedings of the National Academy of Sciences, vol. 105, No. 28, Jul. 15, 2008, pp. 9757-9762.
Wright, G., Terada, K., Yano, M., Sergeev, I. & Mori, M. Oxidative, stress inhibits the mitochondrial import of preproteins and leads to their degradation, *Exp Cell Res* 263, 107-117 (2001).
Wu, L., Grigoryan, A.V., Li, Y., Hao, B., Pagano, M., and Cardozo, T.J., Specific small molecule inhibitors of Skp2-mediated p27 degradation, Chemistry & biology 19, 1515-1524 (2012).
Xu, P., et al. Quantitative proteomics reveals the function of unconventional ubiquitin chains in proteasomal degradation. Cell 137, 133-145 (2009).
Yandim, C., Natisvili, T., and Festenstein, R. (2013). Gene regulation and epigenetics in Friedreich's ataxia. J Neurochem 126 Suppl 1, 21-42.
Yang et al., Design, modification and 3D QSAR studies of novel 2,3-dihydrobenzo[b][1,4]dioxin-containing 4,5-dihydro-1H-pyrazole derivatives as inhibitors of B-Raf kinase, Bioorg. Med. Chem. 20 (2012) 6048-58.
Yang, Y., Ludwig, R.L., Jensen, J.P., Pierre, S.A., Medaglia, M.V., Davydov, I.V., Safiran, Y.J., Oberoi, P., Kenten, J.H., Phillips, A.C. et al. Small molecule inhibitors of HDM2 ubiquitin ligase activity stabilize and activate p53 in cells, Cancer cell 7, 547-559 (2005).
Yonashiro, R. et al., A novel mitochondrial ubiquitin ligase plays a critical role in mitochondrial dynamics, *EMBO J* 25, 3618-3626 (2006).

(56) References Cited

OTHER PUBLICATIONS

Yoon, T. & Cowan, J.A. Iron-sulfur cluster biosynthesis. Characterization of frataxin as an iron donor for assembly of [2Fe—2S] clusters in ISU-type proteins. J Am Chem Soc 125, 6078-6084 (2003).
Yuan et al., One-Pot Synthesis of 3-Hydroxyquinolin-2(1H)-ones from N-Phenylacetoacetamide via $PhI(OCOCF_3)_2$-Mediated α-Hydroxylation and $H_2SO_4$-Promoted Intramolecular Cyclization; Journal of Organic Chemistry, 78(11), 5385-5392; 2013.
Zaky, R.R et al., *Spectrochimica Acta Part A: Molecular and Biomolecular Spectroscopy,* 81, 28-34 (2011).
Zhang, W., and Sidhu, S.S., Development of inhibitors in the ubiquitination cascade, FEBS letters 588, 356-367 (2014).
Zyabrev et al., Zhurnal Organicheskoi Khimii, 30(5), 715-19; 1994.
Allavena C, Katlama C, Cotte L, et al. Long-term efficacy and safety of etravirine-containing regimens in a real-life cohort of treatment-experienced HIV-1-infected patients. Infect Dis (Lond) 2016;48(5):392-398.
Benini M, Fortuni S, Condo I, et al. E3 Ligase RNF126 Directly Ubiquitinates Frataxin, Promoting Its Degradation: Identification of a Potential Therapeutic Target for Friedreich Ataxia. Cell Rep 2017;18(8):2007-2017.
Bradley JL, Blake JC, Chamberlain S, Thomas PK, Cooper JM, Schapira AH. Clinical, biochemical and molecular genetic correlations in Friedreich's ataxia. Hum Mol Genet 2000;9(2):275-282.
Bradley JL, Homayoun S, Hart PE, Schapira AH, Cooper JM. Role of oxidative damage in Friedreich's ataxia. Neurochem Res 2004;29(3):561-567.
Campuzano V, Montermini L, Lutz Y, et al. Frataxin is reduced in Friedreich ataxia patients and is associated with mitochondrial membranes. Hum Mol Genet 1997;6(11):1771-1780.
Chantrel-Groussard K, Geromel V, Puccio H, et al. Disabled early recruitment of antioxidant defenses in Friedreich's ataxia. Hum Mol Genet 2001;10(19):2061-2067.
Cherubini et al., "Src inhibitors modulate frataxin protein levels", Human Molecular Genetics, vol. 24. No. 15, May 6, 2015, pp. 4296-4305.
Chutake YK, Lam CC, Costello WN, Anderson MP, Bidichandani SI. Reversal of epigenetic promoter silencing in Friedreich ataxia by a class I histone deacetylase inhibitor. Nucleic Acids Res 2016;44(11):5095-5104.
Codazzi F, Hu A, Rai M, et al. Friedreich ataxia-induced pluripotent stem cell-derived neurons show a cellular phenotype that is corrected by a benzamide HDAC inhibitor. Hum Mol Genet 2016;25(22):4847-4855.
Das K, Clark AD, Jr., Lewi PJ, et al. Roles of conformational and positional adaptability in structure-based design of TMC125-R165335 (etravirine) and related non-nucleoside reverse transcriptase inhibitors that are highly potent and effective against wild-type and drug-resistant HIV-1 variants. Journal of medicinal chemistry 2004;47(10):2550-2560.
de Bethune MP. Non-nucleoside reverse transcriptase inhibitors (NNRTIs), their discovery, development, and use in the treatment of HIV-1 infection: a review of the last 20 years (1989-2009). Antiviral Res 2010;85(1):75-90.
De Biase I, Chutake YK, Rindler PM, Bidichandani SI. Epigenetic silencing in Friedreich ataxia is associated with depletion of CTCF (CCCTC-binding factor) and antisense transcription. PLoS One 2009;4(11):e7914.
Dimmock et al. CAS: 107: 211450, 1987.
Duraes F, Pinto M, Sousa E. Old Drugs as New Treatments for Neurodegenerative Diseases. Pharmaceuticals (Basel) 2018;11(2).
Durr A, Cossee M, Agid Y, et al. Clinical and genetic abnormalities in patients with Friedreich's ataxia. N Engl J Med 1996;335(16):1169-1175.
Eglen RM. Enzyme fragment complementation: a flexible high throughput screening assay technology. Assay and drug development technologies 2002;1(1 Pt 1):97-104.
Filla A, De Michele G, Cavalcanti F, et al. The relationship between trinucleotide (GAA) repeat length and clinical features in Friedreich ataxia. Am J Hum Genet 1996;59(3):554-560.
Gonzalez-Cabo P, Palau F. Mitochondrial pathophysiology in Friedreich's ataxia. J Neurochem 2013;126 Suppl 1:53-64.
Guillemont J, Pasquier E, Palandjian P, et al. Synthesis of novel diarylpyrimidine analogues and their antiviral activity against human immunodeficiency virus type 1. Journal of medicinal chemistry 2005;48(6):2072-2079.
Harding AE. Friedreich's ataxia: a clinical and genetic study of 90 families with an analysis of early diagnostic criteria and intrafamilial clustering of clinical features. Brain 1981;104(3):589-620.
Hayashi, G.; Shen, Y.; Pedersen, T.L.; Newman, J. W; Pook, M.; Cortopassi, G. (2014) Hum Mo/Genet, 23, 6838-47.
Hebert-Chatelain, E. (2013), Int J Biochem Cell Biol, 45, 90-98.
Hofer, A. and Wenz, T. (2014), Exp Gerontol, 56, 202-20.
Hunter, T. (2007), Mot Cell, 28, 730-38.
Katlama C, Clotet B, Mills A, et al. Efficacy and safety of etravirine at week 96 in treatment-experienced HIV type-1-infected patients in the DUET-1 and DUET-2 trials. Antivir Ther 2010;15(7):1045-1052.
Koeppen AH, Becker AB, Qian J, Feustel PJ. Friedreich Ataxia: Hypoplasia of Spinal Cord and Dorsal Root Ganglia. J Neuropathol Exp Neurol 2017;76(2):101-108.
Koeppen AH, Mazurkiewicz JE. Friedreich ataxia: neuropathology revised. J Neuropathol Exp Neurol 2013;72(2):78-90.
Koeppen AH, Morral JA, Davis AN, et al. The dorsal root ganglion in Friedreich's ataxia. Acta Neuropathol 2009;118(6):763-776.
Koeppen AH, Ramirez RL, Becker AB, et al. The pathogenesis of cardiomyopathy in Friedreich ataxia. PLoS One 2015;10(3):e0116396.
Li L, Shen X, Liu Z, et al. Activation of Frataxin Protein Expression by Antisense Oligonucleotides Targeting the Mutant Expanded Repeat. Nucleic Acid Ther 2018;28(1):23-33.
Libri V, Yandim C, Athanasopoulos S, et al. Epigenetic and neurological effects and safety of high-dose nicotinamide in patients with Friedreich's ataxia: an exploratory, open-label, dose-escalation study. Lancet 2014.
Marmolino D. Friedreich's ataxia: past, present and future. Brain Res Rev 2011;67(1-2):311-330.
Mateo I, Llorca J, Volpini V, Corral J, Berciano J, Combarros O. GAA expansion size and age at onset of Friedreich's ataxia. Neurology 2003;61(2):274-275.
Nelson M, Hill A, van Delft Y, Moecklinghoff C. Etravirine as a Switching Option for Patients with HIV RNA Suppression: A Review of Recent Trials. AIDS Res Treat 2014;2014:636584.
Puccio, H.; Anheim, M.; Tranchant, C. (2014), I, 170, 355-65.
Rai, M., et al., "HDAC Inhibitors Correct Frataxin Deficiency in a Friedreich Ataxia Mouse Model," PLoS ONE, vol. 3, No. 4, pp. 1-8, Apr. 2008.
Sandeo S, Scott BD, McMackin MZ, et al. Dyclonine rescues frataxin deficiency in animal models and buccal cells of patients with Friedreich's ataxia. Hum Mol Genet 2014;23(25):6848-6862.
Santoro A, Anjomani Virmouni S, Paradies E, et al. Effect of diazoxide on Friedreich ataxia models. Hum Mol Genet 2018;27(6):992-1001.
Sardana D, Zhu C, Zhang M, Gudivada RC, Yang L, Jegga AG. Drug repositioning for orphan diseases. Brief Bioinform 2011;12(4):346-356.
Schulz JB, Dehmer T, Schols L, et al. Oxidative stress in patients with Friedreich ataxia. Neurology 2000;55(11):1719-1721.
Shameer K, Readhead B, Dudley JT. Computational and experimental advances in drug repositioning for accelerated therapeutic stratification. Curr Top Med Chem 2015;15(1):5-20.
Soragni E, Gottesfeld JM. Translating HDAC inhibitors in Friedreich's ataxia. Expert Opin Orphan Drugs 2016;4(9):961-970.
Soragni E, Miao W, Iudicello M, Jacoby D, De Mercanti S, Clerico M, Longo F, Piga A, Ku S, Campau E, Du J, Penalver P, Rai M, Madara JC, Nazor K, O'Connor M, Maximov A, Loring JF, Pandolfo M, Durelli L, Gottesfeld JM, Rusche JR. 2014. Epigenetic therapy for Friedreich ataxia. Ann Neurol 76:489-508.
Strawser C, Schadt K, Hauser L, et al. Pharmacological therapeutics in Friedreich ataxia: the present state. Expert review of neurotherapeutics 2017;17(9):895-907.

(56) References Cited

OTHER PUBLICATIONS

Tai G, Corben LA, Yiu EM, Milne SC, Delatycki MB. Progress in the treatment of Friedreich ataxia. Neurol Neurochir Pol 2018;52(2):129-139.
Usach I, Melis V, Peris JE. Non-nucleoside reverse transcriptase inhibitors: a review on pharmacokinetics, pharmacodynamics, safety and tolerability. J Int AIDS Soc 2013;16:1-14.
Wells, J.A. (1990). Additivity of mutational effects in proteins. Biochemistry. 29(37):8509-8517.
Ye H, Rouault TA. Human iron-sulfur cluster assembly, cellular iron homeostasis, and disease. Biochemistry 2010;49(24):4945-4956.

\* cited by examiner

COMPOSITIONS AND METHODS FOR TREATING FRIEDREICH'S ATAXIA

CROSS-REFERENCES TO RELATED APPLICATIONS

This application is a continuation of international application PCT/IB2015/057318 (filed Sep. 22, 2015), which claims the benefit of U.S. Provisional Application No. 62/053,709 (filed Sep. 22, 2014). These applications are incorporated by reference in its entirety for all purposes.

REFERENCE TO A "SEQUENCE LISTING," A TABLE, OR A COMPUTER PROGRAM LISTING APPENDIX SUBMITTED ON A COMPACT DISK

This application includes a Sequence Listing as a text file named SEQ_097459-000110US-0957672_ST25.txt created Sep. 22, 2015, and containing 2,242 bytes. The material contained in this text file is incorporated by reference in its entirety for all purposes.

TECHNICAL FIELD

The present invention relates generally to compositions and methods useful for the treatment of Friedreich's ataxia.

BACKGROUND ART

Friedreich's ataxia (FRDA) affects >20,000 individuals in Caucasian populations. Generally within 10 to 15 years from onset, it leads to loss of deambulation and complete disability, with premature death often caused by cardiac insufficiency.[1] Symptoms usually appear late in the first decade or early in the second decade of life, and include gait instability and general clumsiness. Skeletal abnormalities, such as scoliosis or pes cavus, may be already present. Gait ataxia has both cerebellar and sensory features, involves truncus and limbs, and is progressive and generally unremitting. Swaying is common and, as it becomes more severe, eventually requires constant support and wheelchair use. Dysarthria occurs early in the disease and progress to complete speech impairment. Dysphagia is a late feature and may require artificial feeding. Ventricular hypertrophy characterizes the cardiac picture, and may progressively lead to congestive heart failure and fatal arrhythmias. A significant minority of patients also develop diabetes mellitus, by not yet clearly defined mechanisms.[2]

FRDA is caused by homozygous hyperexpansion of GAA triplets within the first intron of the FXN gene, an highly conserved five-exon gene located on the long arm of human chromosome 9, coding for the protein frataxin. Pathological GAA expansions (from ~70 to >1,000 triplets) result in "sticky" DNA structures and epigenetic changes that severely reduce transcription of the FXN gene. FRDA patients live with 10-30% residual frataxin, the severity of the disease being directly proportional to the number of GAA triplets and to the consequent degree of frataxin reduction. A minority of FRDA patients, so called compound heterozygotes, has pathological GAA expansions on one FXN allele and loss-of-function mutations on the other. Complete loss of frataxin is not compatible with life, in all species examined.[3]

Human frataxin is synthesized as a 210 amino acid (aa) precursor that is rapidly targeted to the mitochondria. Upon entrance into the mitochondria, the frataxin precursor undergoes a two-step proteolytic processing, mediated by the mitochondrial protein peptidase (MPP). The resulting mature frataxin is a 130aa globular polypeptide that mostly resides within the mitochondrial matrix,[4,5] but that can be also found outside the mitochondria,[6,7] where it might interact with and regulate cytosolic aconitase/IRP1.[8] Frataxin may bind iron directly and act either as an iron donor [9,10] or as an iron sensor involved in the proper functioning of the iron-sulphur cluster (ISC) machinery.[11] Frataxin-defective cells have reduced activity of ISC-containing enzymes, a general imbalance in intracellular iron distribution and increased sensitivity to oxidative stress.

There is currently no specific therapy to prevent the progression of the disease.[12] Most therapeutic approaches are aimed at reducing mitochondrial dysfunction and are based on the use of anti-oxidant or iron chelators.[13,14] Beside this, as levels of residual frataxin are crucial in determining the severity of the disease, many efforts have been put in the identification of molecules that increase frataxin transcription.[15,16] However, no studies have been so far reported regarding neither the physiological turnover of this protein in humans, nor any factors that can modulate its stability. Therefore, the comprehension of the molecular mechanisms that regulate frataxin protein stability might provide fundamental information towards the design of new therapeutic approaches.

Although the maturation process of frataxin has been well characterized, no information is available concerning the biology of frataxin degradation. Since the Ubiquitin-Proteasome System (UPS) is the major pathway for regulated intracellular protein degradation in higher eukaryotes, this pathway was investigated for its involvement in the control of frataxin turnover.[17]

DISCLOSURE OF THE INVENTION

In a first aspect, the present invention provides a method of treating Friedreich's ataxia in a subject in need thereof, comprising administering to a subject a therapeutically effective amount of a polycyclic compound or a pharmaceutically acceptable salt, tautomer, or stereoisomer thereof; wherein the polycyclic compound is of a formula selected from the group consisting of:

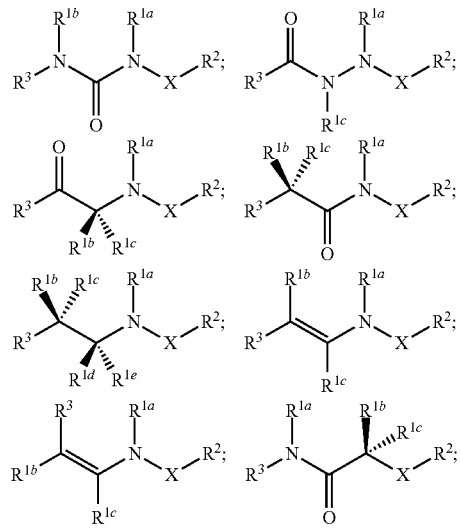

-continued

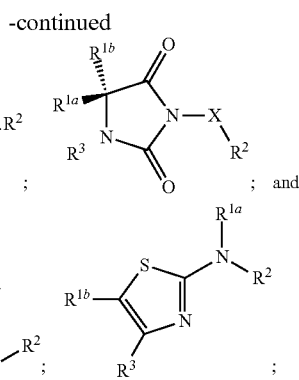
; and

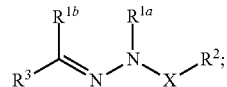
;

wherein:

X is a linking group selected from the group consisting of —S(O)$_2$— and —C(O)—;

$R^{1a}$, $R^{1b}$, $R^{1c}$, $R^{1d}$, and $R^{1e}$ are each independently selected from the group consisting of hydrogen, lower alkyl, fluoroalkyl, aryl, and heteroaryl; wherein the aryl or heteroaryl group has from 0 to 3 $R^4$ substituents;

$R^2$ is a first cyclic group selected from the group consisting of phenyl, naphthyl, and heteroaryl; wherein the $R^2$ group has from 0 to 3 $R^4$ substituents;

$R^3$ is a second cyclic group selected from the group consisting of phenyl, naphthyl, and heteroaryl; wherein the $R^3$ group has from 0 to 4 $R^4$ substituents;

each $R^4$ substituent is independently selected from the group consisting of $C_1$-$C_6$ alkyl, $C_2$-$C_6$ alkenyl, $C_2$-$C_6$ alkynyl, $C_1$-$C_6$ alkoxy, halo, —NO$_2$, —CF$_3$, —CN, —OR$^5$, —SR$^5$, —C(O)R$^5$, —NHC(O)R$^5$, —C(O)OR$^5$, —OC(O)R$^5$, —NR$^5$R$^6$, —C(O)NR$^5$R$^6$, —NHR$^5$C(O)NR$^6$R$^7$, —S(O)$_2$NR$^5$R$^6$, and a cyclic $R^4$ substituent; wherein the cyclic $R^4$ substituent is selected from the group consisting of aryl, heteroaryl, arylalkyl, heteroarylalkyl, cycloalkyl, cycloalkylalkyl, and heterocyclyl; and wherein the cyclic $R^4$ substituent has from 0 to 3 $R^8$ substituents;

each $R^5$, $R^6$, or $R^7$ is independently H, $C_1$-$C_6$ alkyl, $C_2$-$C_6$ alkenyl, $C_2$-$C_6$ alkynyl, $C_1$-$C_6$ alkoxy, halo, or a cyclic $R^5$ substituent; wherein the cyclic $R^5$ substituent is selected from the group consisting of aryl, heteroaryl, arylalkyl, heteroarylalkyl, cycloalkyl, cycloalkylalkyl, and heterocyclyl; and wherein the cyclic $R^5$ substituent has from 0 to 3 $R^8$ substituents; and each $R^8$ is independently $C_1$-$C_6$ alkyl, $C_2$-$C_6$ alkenyl, $C_2$-$C_6$ alkynyl, $C_1$-$C_6$ alkoxy, halo, aryl, heteroaryl, arylalkyl, heteroarylalkyl, cycloalkyl, cycloalkylalkyl, or heterocyclyl; and wherein adjacent $R^4$, $R^5$, $R^6$, or $R^7$ substituents may optionally join to form an additional fused ring selected from the group consisting of aryl, heteroaryl, cycloalkyl, and heterocyclyl; wherein the additional fused ring has from 0 to 3 $R^8$ substituents.

In an alternative first aspect, the present invention provides a method of treating Friedreich's ataxia in a subject in need thereof, comprising administering to a subject a therapeutically effective amount of a polycyclic compound or a pharmaceutically acceptable salt, tautomer, or stereoisomer thereof;

wherein the polycyclic compound is of a formula:

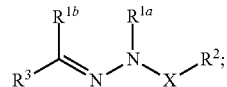

wherein:

X is a linking group selected from the group consisting of —S(O)$_2$— and —C(O)—;

$R^{1a}$ and $R^{1b}$ are each independently selected from the group consisting of hydrogen, lower alkyl, fluoroalkyl, aryl, and heteroaryl; wherein the aryl or heteroaryl group has from 0 to 3 $R^4$ substituents;

$R^2$ is a first cyclic group selected from the group consisting of phenyl, naphthyl, and heteroaryl; wherein the $R^2$ group has from 0 to 3 $R^4$ substituents;

$R^3$ is a second cyclic group selected from the group consisting of phenyl, naphthyl, and heteroaryl; wherein the $R^3$ group has from 0 to 4 $R^4$ substituents;

each $R^4$ substituent is independently selected from the group consisting of $C_1$-$C_6$ alkyl, $C_2$-$C_6$ alkenyl, $C_2$-$C_6$ alkynyl, $C_1$-$C_6$ alkoxy, halo, —NO$_2$, —CF$_3$, —CN, —OR$^5$, —SR$^5$, —C(O)R$^5$, —NHC(O)R$^5$, —C(O)OR$^5$, —OC(O)R$^5$, —NR$^5$R$^6$, —C(O)NR$^5$R$^6$, —NHR$^5$C(O)NR$^6$R$^7$, —S(O)$_2$NR$^5$R$^6$, and a cyclic $R^4$ substituent; wherein the cyclic $R^4$ substituent is selected from the group consisting of aryl, heteroaryl, arylalkyl, heteroarylalkyl, cycloalkyl, cycloalkylalkyl, and heterocyclyl; and wherein the cyclic $R^4$ substituent has from 0 to 3 $R^8$ substituents;

each $R^5$, $R^6$, or $R^7$ is independently H, $C_1$-$C_6$ alkyl, $C_2$-$C_6$ alkenyl, $C_2$-$C_6$ alkynyl, $C_1$-$C_6$ alkoxy, halo, or a cyclic $R^5$ substituent; wherein the cyclic $R^5$ substituent is selected from the group consisting of aryl, heteroaryl, arylalkyl, heteroarylalkyl, cycloalkyl, cycloalkylalkyl, and heterocyclyl; and wherein the cyclic $R^5$ substituent has from 0 to 3 $R^8$ substituents; and each $R^8$ is independently $C_1$-$C_6$ alkyl, $C_2$-$C_6$ alkenyl, $C_2$-$C_6$ alkynyl, $C_1$-$C_6$ alkoxy, halo, aryl, heteroaryl, arylalkyl, heteroarylalkyl, cycloalkyl, cycloalkylalkyl, or heterocyclyl; and wherein adjacent $R^4$, $R^5$, $R^6$, or $R^7$ substituents may optionally join to form an additional fused ring selected from the group consisting of aryl, heteroaryl, cycloalkyl, and heterocyclyl; wherein the additional fused ring has from 0 to 3 $R^8$ substituents.

In some embodiments of either aspect, the method has the proviso that the polycyclic compound is not disclosed in U.S. Pat. No. 8,703,749.

In some preferred embodiments of either aspect, the $R^8$ substituents are unsubstituted (i.e., have no optional substituents).

In some preferred embodiments of either aspect, all components have no optional substitution that is not expressly indicated. For example, if $R^3$ may be a group with from 0 to 4 $R^4$ substituents, and $R^3$ is aryallkyl, $R^3$ has only 0 to 4 substituents even if arylalkyl groups (or their constituent aryl and alkyl groups) are defined as possibly including additional optional substitution.

In some embodiments of either aspect, the polycyclic compound formula is selected from those described in Table 1.

In some embodiments of either aspect, X is —S(O)$_2$—.

In some embodiments of either aspect, X is —C(O)—.

In some embodiments of either aspect, $R^{1a}$, $R^{1b}$, $R^{1c}$, $R^{1d}$, and $R^{1e}$ are each independently selected from the group consisting of hydrogen, lower alkyl, and aryl.

In some embodiments of either aspect, $R^{1a}$, $R^{1b}$, $R^{1c}$, $R^{1d}$, and $R^{1e}$ are each independently selected from the group consisting of hydrogen and lower alkyl.

In some embodiments of either aspect, $R^{1a}$, $R^{1b}$, $R^{1c}$, $R^{1d}$, and $R^{1e}$ are each independently selected from the group consisting of hydrogen, methyl, and phenyl.

In some embodiments of either aspect, $R^2$ is selected from the substituents that are listed in Table 2.

In some embodiments of either aspect, $R^2$ is a phenyl group substituted with from 0 to 3 $R^4$ substituents.

In some embodiments of either aspect, $R^2$ is a naphthyl group substituted with from 0 to 3 $R^4$ substituents.

In some embodiments of either aspect, the $R^4$ substituents for the $R^2$ groups are independently selected from the group consisting of halo, lower alkyl, hydroxyl, and alkoxy.

In some embodiments of either aspect, $R^3$ is an aryl group substituted with from 0 to 3 $R^4$ substituents.

In some embodiments of either aspect, $R^3$ is a heteroaryl group substituted with from 0 to 3 $R^4$ substituents.

In some embodiments of either aspect, $R^3$ is a phenothiazinyl group with from 0 to 3 $R^4$ substituents.

In some embodiments of either aspect, the $R^4$ substituents for the $R^3$ groups are independently selected from the group consisting of halo, lower alkyl, hydroxyl, and alkoxy.

In some embodiments of either aspect, the $R^4$ substituents for the $R^3$ groups are independently selected from those that are listed in Table 2.

In some embodiments of either aspect, each $R^4$, $R^5$, $R^6$, $R^7$, or $R^8$ is independently H, $C_1$-$C_6$ alkyl, halo, —$NO_2$, —$CF_3$, —CN, or $C_1$-$C_6$ alkoxy.

In some embodiments of either aspect, the method of treating Friedreich's ataxia comprises inhibiting ubiquitination of frataxin.

In some embodiments of either aspect, the subject is a mammal.

In some embodiments of either aspect, the mammal is a human.

In a second aspect, the invention provides a method of inhibiting ubiquitination of frataxin in a subject comprising administering to a subject a therapeutically effective amount of a compound as described herein, or a pharmaceutically acceptable salt, tautomer, or stereoisomer thereof.

In some embodiments, at least one $R^4$ is a halogen.

In a third aspect, the invention provides a pharmaceutical composition comprising a therapeutically effective amount of a polycyclic compound or a pharmaceutically acceptable salt, tautomer, or stereoisomer thereof.

wherein the polycyclic compound is of a formula selected from the group consisting of:

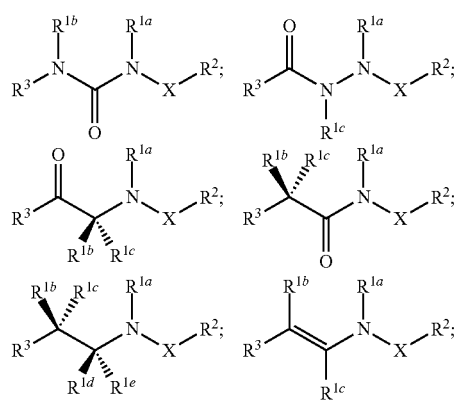

-continued

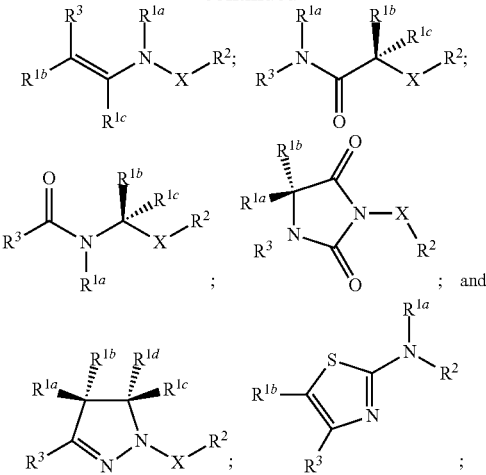

wherein:

X is a linking group selected from the group consisting of —$S(O)_2$— and —C(O)—;

$R^{1a}$, $R^{1b}$, $R^{1c}$, $R^{1d}$, and $R^{1e}$ are each independently selected from the group consisting of hydrogen, lower alkyl, fluoroalkyl, aryl, and heteroaryl; wherein the aryl or heteroaryl group has from 0 to 3 $R^4$ substituents;

$R^2$ is a first cyclic group selected from the group consisting of phenyl, naphthyl, and heteroaryl; wherein the $R^2$ group has from 0 to 3 $R^4$ substituents;

$R^3$ is a second cyclic group selected from the group consisting of phenyl, naphthyl, and heteroaryl; wherein the $R^3$ group has from 0 to 4 $R^4$ substituents;

each $R^4$ substituent is independently selected from the group consisting of $C_1$-$C_6$ alkyl, $C_2$-$C_6$ alkenyl, $C_2$-$C_6$ alkynyl, $C_1$-$C_6$ alkoxy, halo, —$NO_2$, —$CF_3$, —CN, —$OR^5$, —$SR^5$, —$C(O)R^5$, —$NHC(O)R^5$, —$C(O)OR^5$, —$OC(O)R^5$, —$NR^5R^6$, —$C(O)NR^5R^6$, —$NHR^5C(O)NR^6R^7$, —$S(O)_2NR^5R^6$, and a cyclic $R^4$ substituent; wherein the cyclic $R^4$ substituent is selected from the group consisting of aryl, heteroaryl, arylalkyl, heteroarylalkyl, cycloalkyl, cycloalkylalkyl, and heterocyclyl; and wherein the cyclic $R^4$ substituent has from 0 to 3 $R^8$ substituents;

each $R^5$, $R^6$, or $R^7$ is independently H, $C_1$-$C_6$ alkyl, $C_2$-$C_6$ alkenyl, $C_2$-$C_6$ alkynyl, $C_1$-$C_6$ alkoxy, halo, or a cyclic $R^5$ substituent; wherein the cyclic $R^5$ substituent is selected from the group consisting of aryl, heteroaryl, arylalkyl, heteroarylalkyl, cycloalkyl, cycloalkylalkyl, and heterocyclyl; and wherein the cyclic $R^5$ substituent has from 0 to 3 $R^8$ substituents; and each $R^8$ is independently $C_1$-$C_6$ alkyl, $C_2$-$C_6$ alkenyl, $C_2$-$C_6$ alkynyl, $C_1$-$C_6$ alkoxy, halo, aryl, heteroaryl, arylalkyl, heteroarylalkyl, cycloalkyl, cycloalkylalkyl, or heterocyclyl; and wherein adjacent $R^4$, $R^5$, $R^6$, or $R^7$ substituents may optionally join to form an additional fused ring selected from the group consisting of aryl, heteroaryl, cycloalkyl, and heterocyclyl; wherein the additional fused ring has from 0 to 3 $R^8$ substituents.

In an alternative third aspect, the invention provides a pharmaceutical composition comprising a therapeutically effective amount of a polycyclic compound or a pharmaceutically acceptable salt, tautomer, or stereoisomer thereof;

wherein the polycyclic compound is of a formula:

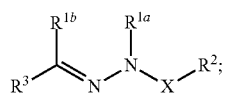

wherein:
X is a linking group selected from the group consisting of —S(O)$_2$— and —C(O)—;
$R^{1a}$ and $R^{1b}$ are each independently selected from the group consisting of hydrogen, lower alkyl, fluoroalkyl, aryl, and heteroaryl; wherein the aryl or heteroaryl group has from 0 to 3 $R^4$ substituents;
$R^2$ is a first cyclic group selected from the group consisting of phenyl, naphthyl, and heteroaryl; wherein the $R^2$ group has from 0 to 3 $R^4$ substituents;
$R^3$ is a second cyclic group selected from the group consisting of phenyl, naphthyl, and heteroaryl; wherein the $R^3$ group has from 0 to 4 $R^4$ substituents;
each $R^4$ substituent is independently selected from the group consisting of $C_1$-$C_6$ alkyl, $C_2$-$C_6$ alkenyl, $C_2$-$C_6$ alkynyl, $C_1$-$C_6$ alkoxy, halo, —NO$_2$, —CF$_3$, —CN, —OR$^5$, —SR$^5$, —C(O)R$^5$, —NHC(O)R$^5$, —C(O)OR$^5$, —OC(O)R$^5$, —NR$^5$R$^6$, —C(O)NR$^5$R$^6$, —NHR$^5$C(O)NR$^6$R$^7$, —S(O)$_2$NR$^5$R$^6$, and a cyclic $R^4$ substituent; wherein the cyclic $R^4$ substituent is selected from the group consisting of aryl, heteroaryl, arylalkyl, heteroarylalkyl, cycloalkyl, cycloalkylalkyl, and heterocyclyl; and wherein the cyclic $R^4$ substituent has from 0 to 3 $R^8$ substituents;
each $R^5$, $R^6$, or $R^7$ is independently H, $C_1$-$C_6$ alkyl, $C_2$-$C_6$ alkenyl, $C_2$-$C_6$ alkynyl, $C_1$-$C_6$ alkoxy, halo, or a cyclic $R^5$ substituent; wherein the cyclic $R^5$ substituent is selected from the group consisting of aryl, heteroaryl, arylalkyl, heteroarylalkyl, cycloalkyl, cycloalkylalkyl, and heterocyclyl; and wherein the cyclic $R^5$ substituent has from 0 to 3 $R^8$ substituents; and
each $R^8$ is independently $C_1$-$C_6$ alkyl, $C_2$-$C_6$ alkenyl, $C_2$-$C_6$ alkynyl, $C_1$-$C_6$ alkoxy, halo, aryl, heteroaryl, arylalkyl, heteroarylalkyl, cycloalkyl, cycloalkylalkyl, or heterocyclyl; and
wherein adjacent $R^4$, $R^5$, $R^6$, or $R^7$ substituents may optionally join to form an additional fused ring selected from the group consisting of aryl, heteroaryl, cycloalkyl, and heterocyclyl; wherein the additional fused ring has from 0 to 3 $R^8$ substituents In some embodiments of either aspect, the method has the proviso that the polycyclic compound is not disclosed in U.S. Pat. No. 8,703,749.

In some embodiments of either aspect, the pharmaceutical compositions of the invention are for use in the methods of treating Friedreich's ataxia described herein. In some embodiments of either aspect, the pharmaceutical compositions of the invention are for use in the methods of inhibiting ubiquitination of frataxin described herein.

BRIEF DESCRIPTION OF THE DRAWINGS

FIG. 1A shows a crystal structure of frataxin with the solvent accessible molecular surface around the W155 pocket. FIG. 1B shows the W155 pocket with the ligand UCM71. FIG. 1C shows selected hydroge bonding interactions of UCM71 with frataxin. FIG. 1D shows the flexibility of the carbonyl-hydrazone scaffold that permits the flip of the phenothiazine moiety to point its central amino group toward Q148.

FIG. 3A shows SDS-PAGE analysis of cell extracts containing frataxin precursor and ubiquitin-conjugate frataxin. FIG. 3B shows the relative ubiquitination levels, quantitated as the densitometric ratio between ubiquitinated frataxin bands and frataxin precursor bands for each MG132-treated lanes.

FIG. 4A shows the SDS-PAGE analysis of cell extracts containing frataxin precursor. FIG. 4B shows the relative frataxin precursor levels as quantitated by densitometric analysis.

FIG. 6A shows the results for the cell line FRDA 798 and a control, FRDA 241. FIG. 6B shows the results for the cell line FRDA 214 and a control, FRDA 215. FIG. 6C shows the significant increase in aconitases activity in FRDA 214 after treatment with UCM108 for 5 days.

BEST MODE FOR CARRYING OUT THE INVENTION

Figure 1A:
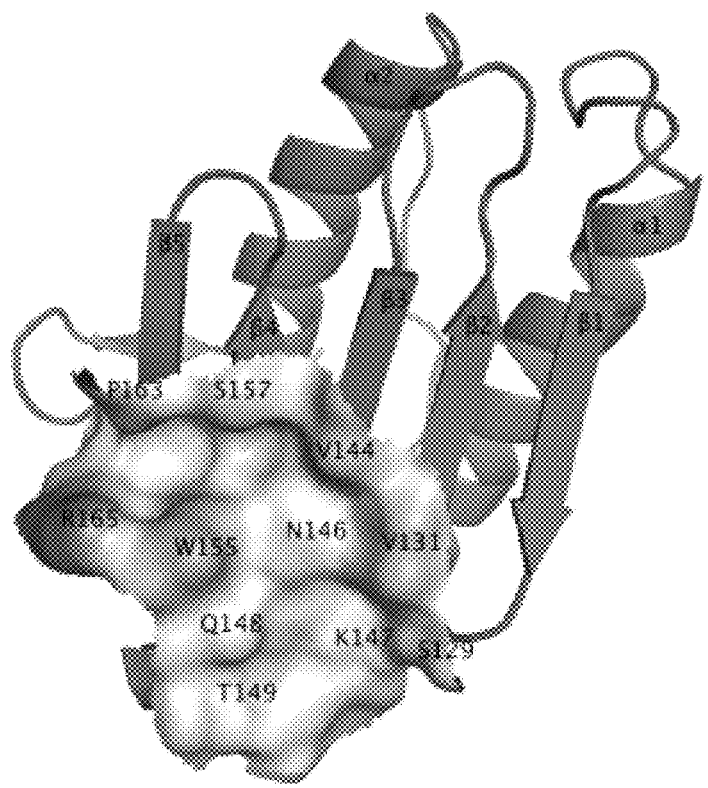
FIGS. 1A-1D show a model of a ubiquitin-competing molecule, UCM71, docking to frataxin.

Described herein are compositions and methods for the treatment of Freidreich's ataxia. The present disclosure relates to the surprising discovery that Freidreich's ataxia can be treated by inhibiting degradation of frataxin by the Ubiquitin-Proteasome System. Frataxin is directly modified by ubiquitin, and lysine[147] is the critical residue responsible for frataxin ubiquitination and subsequent degradation.

Described herein are compounds and methods for treating Friedreich's ataxia. In some aspects, methods of treating Friedreich's ataxia are described, wherein the frataxin molecular pocket harboring lysine[147] is targeted. In further aspects, methods for inhibiting frataxin ubiquitination and degradation are described, wherein the molecular pocket harboring lysine[147] is targeted. In further aspects, methods for increasing frataxin levels are described, wherein the molecular pocket harboring lysine[147] is targeted.

The site of frataxin ubiquitination is at a molecular pocket harboring lysine[147]. In certain aspects, the present disclosure provides a description of the molecular pocket harboring lysine[147]. In further aspects, methods of blocking ubiquitin from accessing the molecular pocket harboring lysine[147] are provided.

In certain aspects, compounds are provided for inhibiting ubiquitin-mediated degradation by targeting the frataxin molecular pocket harboring lysine[147]. The compounds of the present disclosure may be any compound capable of inhibiting ubiquitin-mediated degradation of frataxin by targeting the molecular pocket harboring lysine[147]. In further aspects, the compounds of the present disclosure are used to treat Friedreich's ataxia by binding and blocking the frataxin molecular pocket harboring lysine[147]. In further aspects, the compounds of the present disclosure are used to increase frataxin levels by binding and blocking the frataxin molecular pocket harboring lysine[147].

Definitions

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (2007) "Advanced Organic Chemistry 5$^{th}$ Ed." Vols. A and B, Springer Science+Business Media LLC, New York. The practice of the present invention will employ, unless otherwise indicated, conventional methods of synthetic organic chemistry, X-ray crystallography, protein NMR, mass spectroscopy, protein chemistry, biochemistry, preparative and analytical methods of chromatography, recombinant DNA techniques and pharmacology, within the skill of the art.

Any terms not directly defined herein shall be understood to have the meanings commonly associated with them as understood within the art of the invention. Certain terms are discussed herein to provide additional guidance to the practitioner in describing the compositions, devices, methods and the like of aspects of the invention, and how to make or use them. It will be appreciated that the same thing can be said in more than one way. Consequently, alternative language and synonyms can be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the invention herein.

The term "about" as used herein to modify a numerical value indicates a defined range around that value. If "X" were the value, "about X" would generally indicate a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X." When the quantity "X" only includes whole-integer values (e.g., "X carbons"), "about X" indicates the values X, X−1, and X+1.

When the term "about" is applied to the beginning of a numerical range, it applies to both ends of the range. Thus, "from about 5 to 20%" is equivalent to "from about 5% to about 20%." When "about" is applied to the first value of a set of values, it applies to all values in that set. Thus, "about 7, 9, or 11" is equivalent to "about 7, about 9, or about 11." However, when the modifier "about" is applied to describe only the end of a range or only a later value in a set of values, it applies only to that value or that end of the range. Thus, the range "about 2 to 10" is the same as "about 2 to about 10," but the range "2 to about 10" is not.

The term "alkenyl" as used herein includes substituted or unsubstituted, straight and branched chain alkene radicals, including both the E- and Z-forms, containing from two to eight carbon atoms. The alkenyl group may be optionally substituted with one or more substituents selected from the group consisting of $C_1$-$C_6$ alkyl, $C_2$-$C_6$ alkenyl, $C_2$-$C_6$ alkynyl, $C_1$-$C_6$ alkoxy, halo, aryl, arylalkyl, cycloalkyl, or heterocycle. In some embodiments, the alkenyl group is not optionally substituted. In some embodiments, the alkenyl group has 1, 2, or 3 substituents.

The term "alkyl" as used herein includes substituted or unsubstituted, straight and branched chain alkyl radicals containing from one to fifteen carbon atoms. The alkyl group may be optionally substituted with one or more substituents selected from $C_1$-$C_6$ alkyl, $C_2$-$C_6$ alkenyl, $C_2$-$C_6$ alkynyl, $C_1$-$C_6$ alkoxy, halo, aryl, arylalkyl, cycloalkyl, or heterocycle. In some embodiments, the alkyl group is not optionally substituted. In some embodiments, the alkyl group has 1, 2, or 3 substituents (e.g., trifluoromethyl).

The term "alkoxy" as used herein includes an oxygen with a $C_1$-$C_8$ alkyl group (e.g., $C_1$-$C_6$) group as a substituent and includes methoxy, ethoxy, butoxy, trifluromethoxy and the like. If the alkoxy group is optionally substituted, it also includes divalent substituents linked to two separated oxygen atoms such as, without limitation, —O—$(CH_2)_{1-4}$—O—, —O—$CF_2$—O—, —O—$(CH_2)_{1-4}$—O—$(CH_2CH_2$—$O)_{1-4}$— and —(O—$CH_2CH_2$—$O)_{1-4}$—. In some embodiments, the alkoxy group is not optionally substituted. In some embodiments, the alkoxy group has 1, 2, or 3 substituents, which are preferably fluoro substituents (e.g., trifluoromethoxy).

The term "alkynyl" as used herein includes substituted or unsubstituted, straight and branched carbon chain containing from two to eight carbon atoms and having at least one carbon-carbon triple bond. The term alkynyl includes, for example ethynyl, 1-propynyl, 2- propynyl, 1-butynyl, 3-methyl-1-butynyl and the like. The alkynyl group may be optionally substituted with one or more substituents selected from $C_1$-$C_6$ alkyl, $C_2$-$C_6$ alkenyl, $C_2$-$C_6$ alkynyl, $C_1$-$C_6$ alkoxy, halo, aryl, arylalkyl, cycloalkyl, or heterocycle. In some embodiments, the alkynyl group is not optionally substituted. In some embodiments, the alkynyl group has 1, 2, or 3 substituents.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

Antibodies of the present invention can be described or specified in terms of the epitope(s) or portion(s) of a polypeptide of the present invention which are recognized or specifically bound by the antibody. The epitope(s) or polypeptide portion(s) can be specified as described herein, e.g., by N-terminal and C-terminal positions, by size in contiguous amino acid residues.

The terms "aryl" as used herein includes substituted or unsubstituted single-ring and multiple aromatic groups (for example, phenyl, pyridyl and pyrazole, etc.) and polycyclic ring systems (naphthyl and quinolinyl, etc.). In some embodiments, the aryl group is phenyl or substituted phenyl. The polycyclic rings may have two or more rings in which two atoms are common to two adjoining rings (the rings are "fused") wherein at least one of the rings is aromatic, e.g., the other rings can be cycloalkyls, cycloalkenyls, aryl, heterocycles and/or heteroaryls. The aryl group may be optionally substituted with one or more substituents selected from $C_1$-$C_6$ alkyl, $C_2$-$C_6$ alkenyl, $C_2$-$C_6$ alkynyl, $C_1$-$C_6$ alkoxy, halo, aryl, arylalkyl, cycloalkyl, or heterocycle. In some embodiments, the aryl group is not optionally substituted. In some embodiments, the arylalkyl group has 1, 2, 3, 4, or 5 substituents (e.g., 1, 2, or 3 substituents).

The term "arylalkyl" as used herein includes a $C_1$-$C_6$ alkyl group which has as a substituent an aromatic group, which aromatic group may be substituted or unsubstituted. The aralkyl group may be optionally substituted with one or more substituents selected from $C_1$-$C_6$ alkyl, $C_2$-$C_6$ alkenyl, $C_2$-$C_6$ alkynyl, $C_1$-$C_6$ alkoxy, halo, aryl, arylalkyl, cycloalkyl, or heterocycle. In some embodiments, the arylalkyl group is not optionally substituted. In some embodiments, the arylalkyl group has 1, 2, 3, 4, or 5 substituents on the aryl ring. In some embodiments, the arylalkyl group has 1 or 2 substituents on the $C_1$-$C_6$ alkyl grouping.

The linking term "comprising" or "comprise" as used herein is not closed. For example, "a composition comprising A" must include at least the component A, but it may also include one or more other components (e.g., B; B and C; B, C, and D; and the like).

The term "cycloalkyl" as used herein includes substituted or unsubstituted cyclic alkyl radicals containing from three to twelve carbon atoms and includes cyclopropyl, cyclopentyl, cyclohexyl and the like. The term "cycloalkyl" also includes polycyclic systems having two rings in which two or more atoms are common to two adjoining rings (the rings are "fused"). The cycloalkyl group may be optionally substituted with one or more substituents selected from $C_1$-$C_6$ alkyl, $C_2$-$C_6$ alkenyl, $C_2$-$C_6$ alkynyl, $C_1$-$C_6$ alkoxy, halo, aryl, arylalkyl, cycloalkyl, or heterocycle. In some embodiments, the cycloalkyl group is unsubstituted. In some embodiments, the cycloalkyl group has 1, 2, 3, 4, or 5 substitutents. In some embodiments, the cycloalkyl group has 1, 2, or 3 substitutents.

The term "fluoroalkyl" as used herein includes an alkyl group with at least one fluoro substituent. Examples include trifluoromethyl and difluoromethyl. In some embodiments, the fluoroalkyl group has only fluoro or hydrogen substituents. In some embodiments, the fluoroalkyl group has 1, 2, or 3 other substituents.

The term "halo" or "halogen" as used herein includes fluorine, chlorine, bromine and iodine. In some embodiments, the halo group is chlorine or bromine. In some embodiments, the halo group is fluorine.

The term "heterocycle" or "heterocyclic" as used herein includes substituted or unsubstituted aromatic and non-aromatic cyclic radicals having at least one heteroatom as a ring member. Preferred heterocyclic groups are those containing five or six ring atoms that include at least one hetero atom, which may include cyclic amines such as morpholino, piperidino, pyrrolidino and the like; and cyclic ethers, such as tetrahydrofuran, tetrahydropyran and the like. Aromatic heterocyclic groups, also termed "heteroaryl" groups, includes single-ring hetero-aromatic groups that may include from one to three heteroatoms, for example, pyrrole, furan, thiophene, imidazole, oxazole, thiazole, triazole, pyrazole, oxodiazole, thiadiazole, pyridine, pyrazine, pyridazine, pyrimidine and the like. The term heteroaryl also includes polycyclic hetero-aromatic systems having two or more rings in which two or more atoms are common to two adjoining rings (the rings are "fused") wherein at least one of the rings is a heteroaryl, e.g., the other rings can be cycloalkyls, cycloalkenyls, aryl, heterocycles and/or heteroaryls. Examples of polycyclic heteroaromatic systems include quinoline, isoquinoline, cinnoline, tetrahydroisoquinoline, quinoxaline, quinazoline, benzimidazole, benzofuran, benzothiophene, benzoxazole, benzothiazole, indazole, purine, benzotriazole, pyrrolepyridine, pyrrazolopyridine and the like. The heterocyclic group may be optionally substituted with one or more substituents selected from the group consisting of $C_1$-$C_6$ alkyl, $C_2$-$C_6$ alkenyl, $C_2$-$C_6$ alkynyl, $C_1$-$C_6$ alkoxy, halo, aryl, arylalkyl, cycloalkyl, or heterocycle. In some embodiments, the heterocyclic group is unsubstituted. In some embodiments, the heterocyclic group has 1, 2, 3, 4, or 5 substitutents. In some embodiments, the heterocyclic group has 1, 2, or 3 substitutents.

When any two substituent groups or any two instances of the same substituent group are "independently selected" from a list of alternatives, the groups may be the same or different. For example, if $R^a$ and $R^b$ are independently selected from the group consisting of alkyl, fluoro, amino, and hydroxyalkyl, then a molecule with two $R^a$ groups and two $R^b$ groups could have all groups be alkyl group (e.g., four different alkyl groups). Alternatively, the first $R^a$ could be alkyl, the second $R^a$ could be fluoro, the first $R^b$ could be hydroxyalkyl, and the second $R^b$ could be amino (or any other substituents taken from the group). Alternatively, both Ra and the first $R^b$ could be fluoro, while the second $R^b$ could be alkyl (i.e., some pairs of substituent groups may be the same, while other pairs may be different).

As used herein to refer to a substiuent, "lower" refers to a substituent containing one to six carbons (i.e., "$C_1$-$C_6$," which is used interchangeably).

As used herein, "or" should in general be construed non-exclusively. For example, an embodiment of "a composition comprising A or B" would typically present an aspect with a composition comprising both A and B. "Or" should, however, be construed to exclude those aspects presented that cannot be combined without contradiction (e.g., a composition pH that is between 9 and 10 or between 7 and 8).

"Pharmaceutically acceptable salt" refers to a salt of a compound of the invention which is made with counterions understood in the art to be generally acceptable for pharmaceutical uses and which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-l-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, morpholine, piperidine, dimethylamine, diethylamine and the like. Also included are salts of amino acids such as arginates and the like, and salts of organic acids like glucurmic or galactunoric acids and the like (see, e.g., Berge et al., 1977, *J. Pharm. Sci.* 66:1-19).

"Specific binding" refers to the ability of two molecules to bind to each other in preference to binding to other molecules in the environment. Typically, "specific binding" discriminates over adventitious binding in a reaction by at least two-fold, more typically by at least 10-fold, often at least 100-fold. Typically, the affinity or avidity of a specific binding reaction, as quantified by a dissociation constant, is about $10^{-7}$ M or stronger (e.g., about $10^{-8}$ M, $10^{-9}$ M or even stronger).

In the Summary of the Invention above, Modes, and the claims below, reference is made to particular features and aspects of the invention, including method steps. The disclosure of the invention in this specification includes all possible combinations of such particular features within the embodiments of the invention disclosed, at least to the extent that such combinations are non-contradictory. For example, if the Detailed Description presents an aspect with embodiments A, B, and C, it is understood that this discloses combined, more specific embodiments that include both aspects A and B, both aspects B and C, and both aspects A and C, as well as an embodiment with the features of A, B, and C.

Methods for Treating Friedrich's Ataxia

In a first aspect, the invention provides a method of treating Friedreich's ataxia in a subject in need thereof, comprising administering to a subject a therapeutically effective amount of a polycyclic compound or a pharmaceutically acceptable salt, tautomer, or stereoisomer thereof; wherein the polycyclic compound is of a formula selected from the group consisting of:

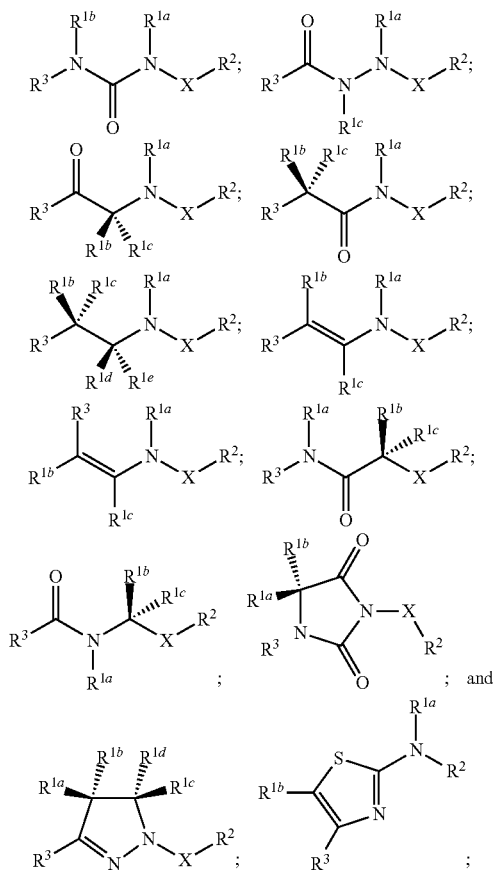

wherein:
X is a linking group selected from the group consisting of —S(O)$_2$— and —C(O)—;

$R^{1a}$, $R^{1b}$, $R^{1c}$, $R^{1d}$, and $R^{1e}$ are each independently selected from the group consisting of hydrogen, lower alkyl, fluoroalkyl, aryl, and heteroaryl; wherein the aryl or heteroaryl group has from 0 to 3 $R^4$ substituents;

$R^2$ is a first cyclic group selected from the group consisting of phenyl, naphthyl, and heteroaryl; wherein the $R^2$ group has from 0 to 3 $R^4$ substituents;

$R^3$ is a second cyclic group selected from the group consisting of phenyl, naphthyl, and heteroaryl; wherein the $R^3$ group has from 0 to 4 $R^4$ substituents;

each $R^4$ substituent is independently selected from the group consisting of $C_1$-$C_6$ alkyl, $C_2$-$C_6$ alkenyl, $C_2$-$C_6$ alkynyl, $C_1$-$C_6$ alkoxy, halo, —NO$_2$, —CF$_3$, —CN, —OR$^5$, —SR$^5$, —C(O)R$^5$, —NHC(O)R$^5$, —C(O)OR$^5$, —OC(O)R$^5$, —NR$^5$R$^6$, —C(O)NR$^5$R$^6$, —NHR$^5$C(O)NR$^6$R$^7$, —S(O)$_2$NR$^5$R$^6$, and a cyclic $R^4$ substituent; wherein the cyclic $R^4$ substituent is selected from the group consisting of aryl, heteroaryl, arylalkyl, heteroarylalkyl, cycloalkyl, cycloalkylalkyl, and heterocyclyl; and wherein the cyclic $R^4$ substituent has from 0 to 3 $R^8$ substituents;

each $R^5$, $R^6$, or $R^7$ is independently H, $C_1$-$C_6$ alkyl, $C_2$-$C_6$ alkenyl, $C_2$-$C_6$ alkynyl, $C_1$-$C_6$ alkoxy, halo, or a cyclic $R^5$ substituent; wherein the cyclic $R^5$ substituent is selected from the group consisting of aryl, heteroaryl, arylalkyl, heteroarylalkyl, cycloalkyl, cycloalkylalkyl, and heterocyclyl; and wherein the cyclic $R^5$ substituent has from 0 to 3 $R^8$ substituents; and each $R^8$ is independently $C_1$-$C_6$ alkyl, $C_2$-$C_6$ alkenyl, $C_2$-$C_6$ alkynyl, $C_1$-$C_6$ alkoxy, halo, aryl, heteroaryl, arylalkyl, heteroarylalkyl, cycloalkyl, cycloalkylalkyl, or heterocyclyl; and wherein adjacent $R^4$, $R^5$, $R^6$, or $R^7$ substituents may optionally join to form an additional fused ring selected from the group consisting of aryl, heteroaryl, cycloalkyl, and heterocyclyl; wherein the additional fused ring has from 0 to 3 $R^8$ substituents.

In some embodiments, the polycyclic compound formula is selected from those described in Table 1.

Examplary compounds to be used with the disclosed methods have been identified through the screening methods disclosed herein. These compounds include the structures set forth in Table 1.

TABLE 1

Exemplary Bridges

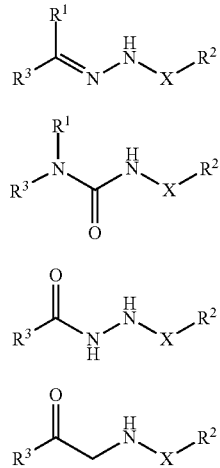

TABLE 1-continued

Exemplary Bridges

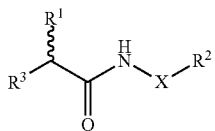

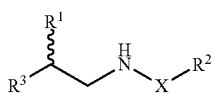

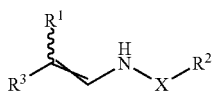

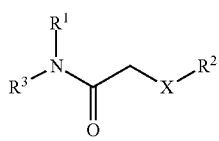

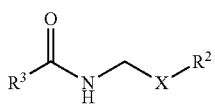

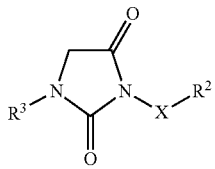

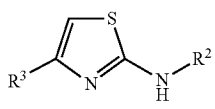

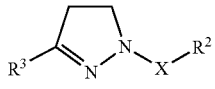

In an alternative first aspect, the present invention provides a method of treating Friedreich's ataxia in a subject in need thereof, comprising administering to a subject a therapeutically effective amount of a polycyclic compound or a pharmaceutically acceptable salt, tautomer, or stereoisomer thereof;

wherein the polycyclic compound is of a formula:

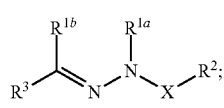

wherein:

X is a linking group selected from the group consisting of —S(O)$_2$— and —C(O)—;

$R^{1a}$ and $R^{1b}$ are each independently selected from the group consisting of hydrogen, lower alkyl, fluoroalkyl, aryl, and heteroaryl; wherein the aryl or heteroaryl group has from 0 to 3 $R^4$ substituents;

$R^2$ is a first cyclic group selected from the group consisting of phenyl, naphthyl, and heteroaryl; wherein the $R^2$ group has from 0 to 3 $R^4$ substituents;

$R^3$ is a second cyclic group selected from the group consisting of phenyl, naphthyl, and heteroaryl; wherein the $R^3$ group has from 0 to 4 $R^4$ substituents;

each $R^4$ substituent is independently selected from the group consisting of $C_1$-$C_6$ alkyl, $C_2$-$C_6$ alkenyl, $C_2$-$C_6$ alkynyl, $C_1$-$C_6$ alkoxy, halo, —NO$_2$, —CF$_3$, —CN, —OR$^5$, —SR$^5$, —C(O)R$^5$, —NHC(O)R$^5$, —C(O)OR$^5$, —OC(O)R$^5$, —NR$^5$R$^6$, —C(O)NR$^5$R$^6$, —NHR$^5$C(O)NR$^6$R$^7$, —S(O)$_2$NR$^5$R$^6$, and a cyclic $R^4$ substituent; wherein the cyclic $R^4$ substituent is selected from the group consisting of aryl, heteroaryl, arylalkyl, heteroarylalkyl, cycloalkyl, cycloalkylalkyl, and heterocyclyl; and wherein the cyclic $R^4$ substituent has from 0 to 3 $R^8$ substituents;

each $R^5$, $R^6$, or $R^7$ is independently H, $C_1$-$C_6$ alkyl, $C_2$-$C_6$ alkenyl, $C_2$-$C_6$ alkynyl, $C_1$-$C_6$ alkoxy, halo, or a cyclic $R^5$ substituent; wherein the cyclic $R^5$ substituent is selected from the group consisting of aryl, heteroaryl, arylalkyl, heteroarylalkyl, cycloalkyl, cycloalkylalkyl, and heterocyclyl; and wherein the cyclic $R^5$ substituent has from 0 to 3 $R^8$ substituents; and each $R^8$ is independently $C_1$-$C_6$ alkyl, $C_2$-$C_6$ alkenyl, $C_2$-$C_6$ alkynyl, $C_1$-$C_6$ alkoxy, halo, aryl, heteroaryl, arylalkyl, heteroarylalkyl, cycloalkyl, cycloalkylalkyl, or heterocyclyl; and wherein adjacent $R^4$, $R^5$, $R^6$, or $R^7$ substituents may optionally join to form an additional fused ring selected from the group consisting of aryl, heteroaryl, cycloalkyl, and heterocyclyl; wherein the additional fused ring has from 0 to 3 $R^8$ substituents.

In some embodiments of either aspect, the method has the proviso that the polycyclic compound is not disclosed in U.S. Pat. No. 8,703,749.

In some embodiments of either aspect, X is —S(O)$_2$—.

In some embodiments of either aspect, X is —C(O)—.

In some embodiments of either aspect, $R^{1a}$, $R^{1b}$, $R^{1c}$, $R^{1d}$, and $R^{1e}$ are each independently selected from the group consisting of hydrogen, lower alkyl, and aryl.

In some embodiments of either aspect, $R^{1a}$, $R^{1b}$, $R^{1c}$, $R^{1d}$, and $R^{1e}$ are each independently selected from the group consisting of hydrogen and lower alkyl.

In some embodiments of either aspect, $R^{1a}$, $R^{1b}$, $R^{1c}$, $R^{1d}$, and $R^{1e}$ are each independently selected from the group consisting of hydrogen, methyl, and phenyl.

In some embodiments of either aspect, $R^2$ is selected from the substituents that are listed in Table 2.

TABLE 2

Compound Substituents

R³\C(R¹)=N-NH-X-R²

| ENTRY | R³ | R¹ | X | R² |
|---|---|---|---|---|
| 1 | 2-phenothiazinyl | H | C(=O) | 6-methyl-2-naphthyl |
| 2 | 4-cyanophenyl | —CH₃ | S(O)₂ | 3-hydroxy-2-naphthyl (methyl-substituted) |
| 3 | 6-methyl-3-oxo-3,4-dihydro-2H-benzo[b][1,4]oxazinyl | | phenyl | 2,6-dihydroxy-3-naphthyl (methyl-substituted) |
| 4 | 6-methyl-5,6,7,8-tetrahydronaphthyl | | | 6-hydroxy-2-naphthyl |
| 5 | 6-methoxy-2-naphthyl | | | 1-methylphthalazinyl |
| 6 | 6-methylbenzo[d][1,3]dioxolyl | | | 3-methyl-1H-indolyl |
| 7 | phenyl | | | 1-methyl-2-(trifluoromethyl)-1H-benzimidazolyl |
| 8 | 4-nitrophenyl | | | 6-methyl-2-naphthyl |
| 9 | 4-aminophenyl | | | phenyl |
| 10 | H₃C— | | | 3-hydroxyphenyl |

TABLE 2-continued

Compound Substituents $$R^3 \underset{R^1}{\overset{}{\text{C}}}=N-\underset{H}{\overset{H}{\text{N}}}-X-R_2$$

| ENTRY | R³ | R¹ | X | R² |
|---|---|---|---|---|
| 11 | 4-(1H-pyrrol-1-yl)phenyl (methyl) | | | 2-fluorophenyl |
| 12 | 4-(benzamido)phenyl (methyl) | | | 2-hydroxyphenyl |
| 13 | 4-(2-nitrophenylamino)phenyl (methyl) | | | phenylethyl (benzyl-CH₂) |
| 14 | N-(4-hydroxy-3-methylphenyl)butyramide derivative | | | 2-chlorophenyl |
| 15 | 1H-indol-3-yl (methyl) | | | 4-methylphenyl |
| 16 | 4-carboxyphenyl (methyl) | | | 4-ethylphenyl |
| 17 | 4-morpholinophenyl (methyl) | | | 4-(trifluoromethyl)phenyl |
| 18 | 1-hydroxy-2-naphthyl (methyl) | | | 4-methoxyphenyl |
| 19 | 2,4-dihydroxyphenyl (methyl) | | | 4-tert-butylphenyl |

TABLE 2-continued

Compound Substituents $$R^3\underset{N}{\overset{R^1}{=}}\overset{H}{\underset{}{N}}-X-R_2$$

| ENTRY | R³ | R¹ | X | R² |
|---|---|---|---|---|
| 20 | 9-ethyl-3-methylcarbazol-3-yl | | | 4-chlorophenyl |
| 21 | 2-hydroxy-3-methyl-5-nitro-... (2-OH, 3-Me, phenyl with O₂N and NO₂) | | | 4-fluorophenyl |
| 22 | 2-hydroxy-3-nitrophenyl (with methyl) | | | 4-bromophenyl |
| 23 | 3,4-dihydroxyphenyl (methyl) | | | 4-ethoxyphenyl |
| 24 | 2-(trifluoromethyl)phenyl | | | 2,4-dimethylphenyl |
| 25 | 3-(trifluoromethyl)phenyl | | | 3,4-dimethylphenyl |
| 26 | 2-chloro-N-(3-methylphenyl)benzamide | | | 2,4-dimethylphenyl |
| 27 | naphthalen-2-yl | | | 2,4-dimethylphenyl |

TABLE 2-continued

Compound Substituents $$R^3\underset{}{\overset{R^1}{=}}N-\underset{H}{N}-X-R_2$$

| ENTRY | R³ | R¹ | X | R² |
|---|---|---|---|---|
| 28 | 3-methyl-1,2-benzenediol | | | 2-methyl-6-nitro-4-(trifluoromethyl)phenyl |
| 29 | 2-methylbenzene-1,4-diol | | | 4-chloro-3-methyl-(trifluoromethyl)phenyl |
| 30 | N-(3-methylphenyl)pyridine-3-carboxamide | | | 4-chloro-3-methyl-methoxyphenyl |
| 31 | 2,3,4-trimethoxy-6-methylphenyl | | | 2-methoxy-6-methylphenyl |
| 32 | 2,4,5-trimethoxy-6-methylphenyl | | | 4-methoxy-2,5-dimethylphenyl |
| 33 | 3-chloro-N-(3-methylphenyl)benzamide | | | 4-methoxy-2,5-dimethylphenyl |
| 34 | 4-methoxy-N-(4-methylphenyl)benzamide | | | 4-chloro-2-methoxy-5-methylphenyl |
| 35 | 1-methylnaphthyl | | | 4-fluoro-2-methoxy-5-methylphenyl |

TABLE 2-continued

Compound Substituents

| ENTRY | R³ | R¹ | X | R² |
|---|---|---|---|---|
| 36 | 2,3,4-trihydroxy-6-methylphenyl | | | |
| 37 | 2-hydroxy-3-methoxy-6-methylphenyl | | | |
| 38 | 4-methoxyphenyl | | | |
| 39 | 4-benzoylphenyl | | | |
| 40 | 2-biphenylyl | | | |
| 41 | 2-(9,10-anthraquinonyl) | | | |
| 42 | 2-(9(10H)-acridonyl) | | | |
| 43 | 4-biphenylyl | | | |

TABLE 2-continued

Compound Substituents $$\underset{R^3}{\overset{R^1}{\underset{N}{\bigvee}}}\underset{X}{\overset{H}{\underset{N}{\bigvee}}}R_2$$

| ENTRY | R³ | R¹ | X | R² |
|---|---|---|---|---|
| 44 | 2-nitro-4-iodo-6-methylphenol (OH, O₂N, I, methyl substituents) | | | |
| 45 | 4-nitro-2-methylphenol (OH, NO₂, methyl) | | | |
| 46 | 2-methylquinoxalin-3-yl | | | |
| 47 | 2-ethoxy-6-methylphenol (OH, H₃CH₂CO, methyl) | | | |

In some embodiments of either aspect, $R^2$ is a phenyl group substituted with from 0 to 3 $R^4$ substituents.

In some embodiments of either aspect, $R^2$ is a naphthyl group substituted with from 0 to 3 $R^4$ substituents.

In some embodiments of either aspect, the $R^4$ substituents for the $R^2$ groups are independently selected from the group consisting of halo, lower alkyl, hydroxyl, and alkoxy.

In some embodiments of either aspect, $R^3$ is an aryl group substituted with from 0 to 3 $R^4$ substituents. In some embodiments of either aspect, $R^3$ is 1,2,3,4-tetrahydronaphthalen-6-yl or 2-methoxynaphthalen-6-yl. In some embodiments of either aspect, $R^3$ is 4-cyanophenyl.

In some embodiments of either aspect, $R^3$ is a heteroaryl group substituted with from 0 to 3 $R^4$ substituents. In some embodiments of either aspect, $R^3$ is 3-oxo-3,4-dihydro-2H-benzo[b][1,4]oxazin-6-yl.

In some embodiments of either aspect, $R^3$ is a phenothiazinyl group with from 0 to 3 $R^4$ substituents. In some embodiments, $R^3$ is 10,10a-dihydro-4aH-phenothiazin-2-yl.

In some embodiments of either aspect, the $R^4$ substituents for the $R^3$ groups are independently selected from the group consisting of halo, lower alkyl, hydroxyl, and alkoxy.

In some embodiments of either aspect, the $R^4$ substituents for the $R^3$ groups are independently selected from those that are listed in Table 2.

In some embodiments of either aspect, each $R^4$ substituent is independently selected from the group consisting of $C_1$-$C_6$ alkyl, $C_2$-$C_6$ alkenyl, $C_2$-$C_6$ alkynyl, $C_1$-$C_6$ alkoxy, halo, —NO₂, —CF₃, —CN, —OR⁵, —SR⁵, —S(O)R⁵, —S(O)₂R⁵, —C(O)R⁵, —NHC(O)R⁵, —C(O)OR⁵, —OC(O)R⁵, —NR⁵R⁶, —C(O)NR⁵R⁶, —NHR⁵C(O)NR⁶R⁷, —S(O)₂NR⁵R⁶, and a cyclic $R^4$ substituent; wherein the cyclic $R^4$ substituent is selected from the group consisting of aryl, heteroaryl, arylalkyl, heteroarylalkyl, cycloalkyl, cycloalkylalkyl, and heterocyclyl; and wherein the cyclic $R^4$ substituent has from 0 to 3 $R^8$ substituents.

In some embodiments of either aspect, each $R^4$, $R^5$, $R^6$, $R^7$, or $R^8$ is independently H, $C_1$-$C_6$ alkyl, halo, —NO₂, —CF₃, —CN, or $C_1$-$C_6$ alkoxy.

In some embodiments of either aspect, at least one $R^4$ is a halogen. In some embodiments of either aspect, at least one $R^4$ is —CN. In some embodiments of either aspect, at least one $R^4$ is a $C_1$-$C_6$ alkoxy (e.g., methoxy).

Certain of the compounds useful in the disclosed methods undergo tautomerization. In those instances, the tautomers of the compounds are included within the scope compounds of disclosed formula I.

In one embodiment, the compound core structure is as in Table 2; $R^1$ is $C_1$-$C_6$ alkyl (e.g., methyl); $R^2$ is phenyl with 0 to 3 $R^4$ substituents (e.g., 2-methoxyphenyl); $R^3$ is a phenothiazinyl group with from 0 to 3 $R^4$ substituents (e.g., $R^3$ in entry 1 of Table 2); and X is (C═O).

In one preferred embodiment, the compound is UCM166:

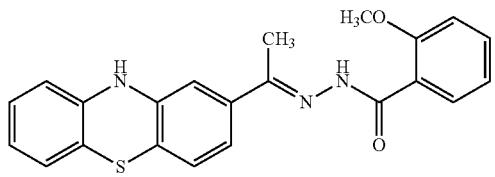

In some embodiments of either aspect, the method of treating Friedreich's ataxia comprises inhibiting ubiquitination of frataxin.

In some embodiments of either aspect, the subject is a mammal.

In some embodiments of either aspect, the mammal is a human.

Methods for Inhibiting the Ubiquitination of Frataxin

In a second aspect, the invention provides a method of inhibiting ubiquitination of frataxin in a subject comprising administering to the subject a therapeutically effective amount of a compound as described herein, or a pharmaceutically acceptable salt, tautomer, or stereoisomer thereof. In some embodiments, the compound is selected from Table 1, Table 2, or Table 3.

In embodiments, at least one $R^4$ is a halogen.

In some embodiments, inhibiting the ubiquitination of frataxin comprises blocking binding by ubiquitin of lysine 147 of frataxin, wherein frataxin has the sequence of SEQ ID NO:1 as disclosed in U.S. Pat. No. 8,703,749.

In some aspects, the compounds disclosed with respect to either first aspect inhibit ubiquitin-mediated degradation by binding and blocking the frataxin molecular pocket harboring lysine[147]. In further aspects, these compounds are used to treat Friedreich's ataxia by binding and blocking the frataxin molecular pocket harboring lysine[147]. In further aspects, these compounds are used to increase frataxin levels by binding and blocking the frataxin molecular pocket harboring lysine[147].

Methods for Preparing Compounds for Treating Friedreich's Ataxia and/or Inhibiting Ubiquitination of Frataxin The compounds used in the methods of the invention can be synthesized via the routes shown in Schemes 1-20. One of skill in the art will appreciate, however, that other well-known methods for preparing the compounds can be used. Such methods are described, for example, in March's *Advanced Organic Chemistry* (John Wiley and Sons, 6th Edition, 2007) and Larock's *Comprehensive Organic Transformations* (VCH Publishers Inc., 1989).

Scheme 1.1

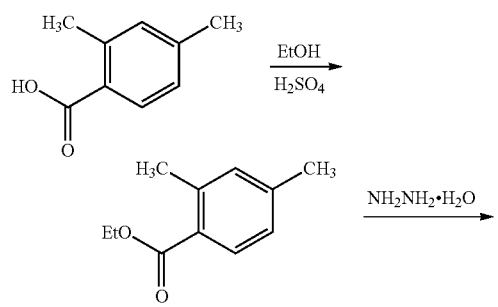

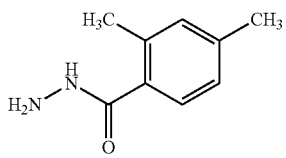

Scheme 1.2

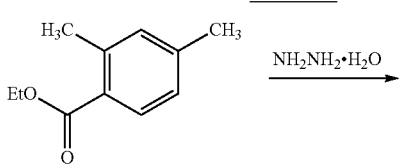

Scheme 1.3

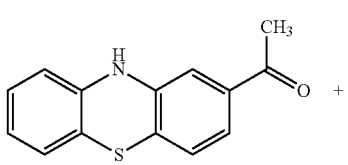

Scheme 2
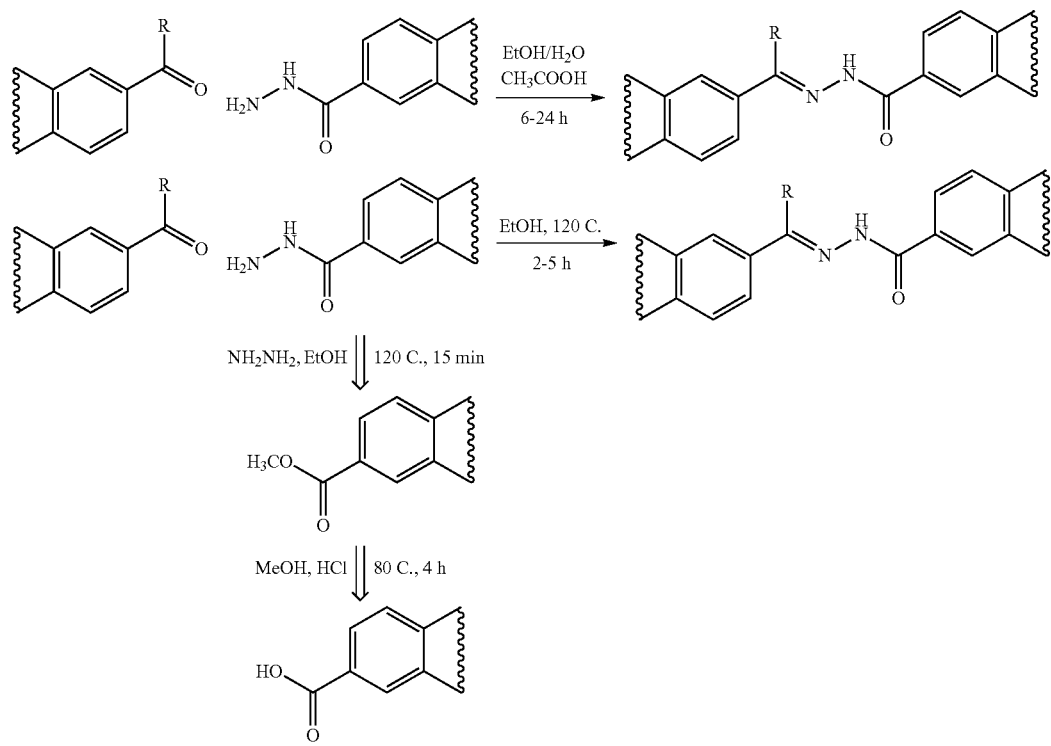
R = H, CH₃, Phenyl
Scheme 3
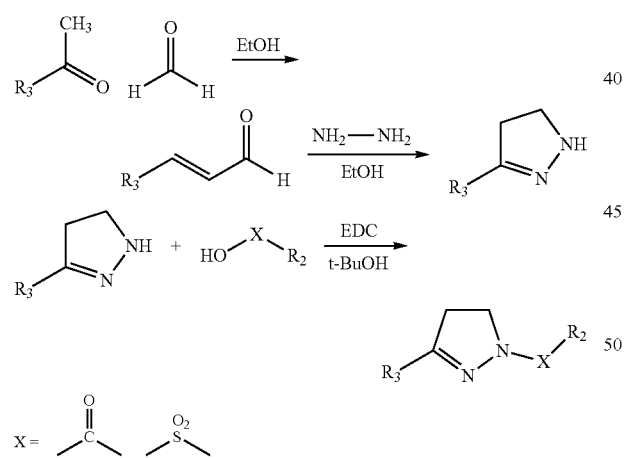
The reactions in Scheme 3 can be conducted according to methods described by Yang et al. [Bioorg. Med. Chem. 20 (2012) 6048-58].
Scheme 4
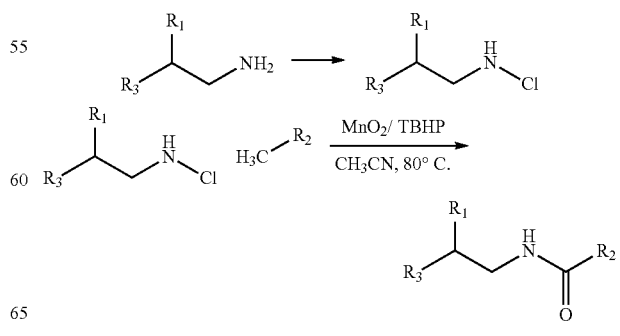
The reactions in Scheme 4 can be conducted according to methods described by Luckhurst et al. [Tetrahedron Letters 48 (2007) 8878-8882] and Chatterjee et al. [Angewandte Chemie 52 (1) (2013) 254-69].
Scheme 5

The reactions in Scheme 5 can be conducted according to methods described by Ghorbani-Vaghei et al. [Synthesis, (6), 945-50; 2009] and Vanjari [*Org. Lett.*, Vol. 15, No. 18, 2013].

Scheme 6

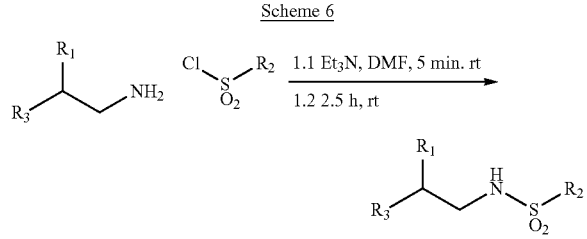

The reactions in Scheme 6 can be conducted according to methods described by Castells Boliart et al. [U.S. Pat. Appl. Publ., 2012/0149909].

Scheme 7

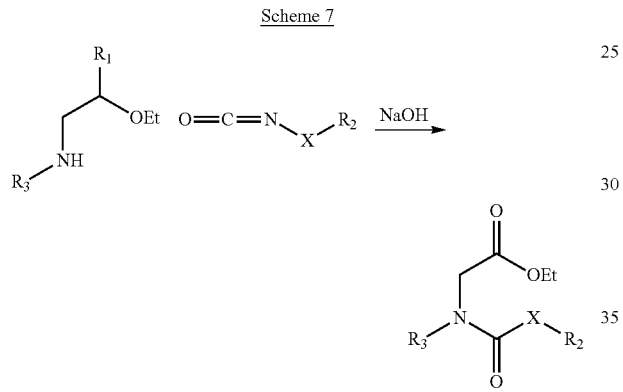

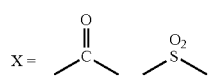

The reactions in Scheme 7 can be conducted according to methods described by Niwata et al. [*J. Med. Chem.*, 1997, Vol. 40, No. 14, 2156-63].

Scheme 8

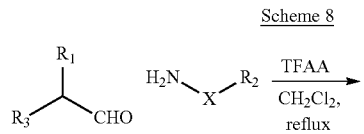

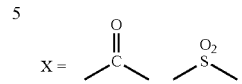

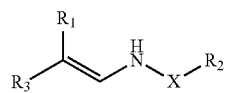

The reactions in Scheme 8 can be conducted according to methods described by Lee et al. [Tetrahedron Letters 44 (2003) 1231-34].

Scheme 9

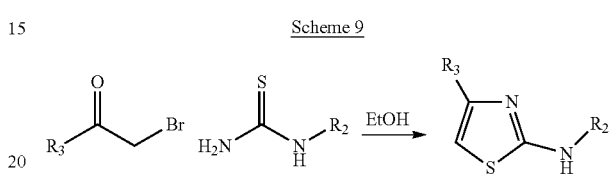

The reactions in Scheme 9 can be conducted according to methods described by Cuconati et al. [PCT Int. Appl., 2013/052613].

Scheme 10

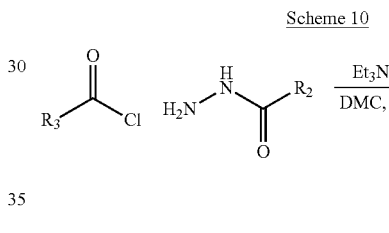

The reactions in Scheme 10 can be conducted according to methods described by

Boström et al. [*J. Med. Chem.* 2012, 55, 1817-30].

Scheme 11

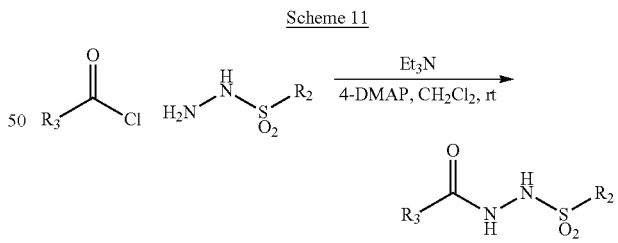

The reactions in Scheme 11 can be conducted according to methods described by Bocanegra-Garcia et al. [Medicinal Chemistry, 8(6), 1039-44; 2012].

Scheme 12

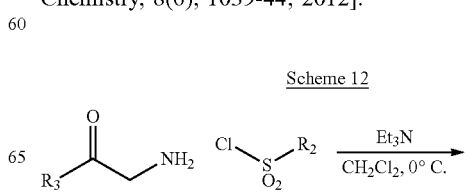

-continued

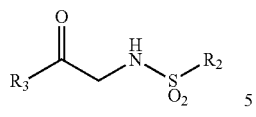

The reactions in Scheme 12 can be conducted according to methods described by Xiang et al. [U.S. Pat. Appl. Publ., 20060025445, 2 Feb. 2006].

Scheme 13

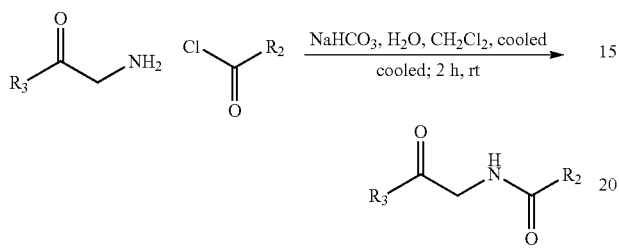

The reactions in Scheme 13 can be conducted according to methods described by Lakner et al. [Synthesis, (12), 1987-1990; 2009].

Scheme 14

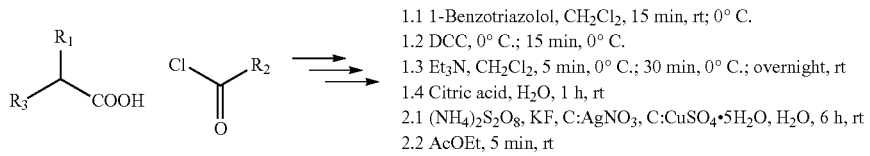

1.1 1-Benzotriazolol, CH$_2$Cl$_2$, 15 min, rt; 0° C.
1.2 DCC, 0° C.; 15 min, 0° C.
1.3 Et$_3$N, CH$_2$Cl$_2$, 5 min, 0° C.; 30 min, 0° C.; overnight, rt
1.4 Citric acid, H$_2$O, 1 h, rt
2.1 (NH$_4$)$_2$S$_2$O$_8$, KF, C:AgNO$_3$, C:CuSO$_4$·5H$_2$O, H$_2$O, 6 h, rt
2.2 AcOEt, 5 min, rt The reactions in Scheme 14 can be conducted according to methods described by Huang and Xu [Journal of Chemical Research, 37(2), 77-79; 2013].

Scheme 15

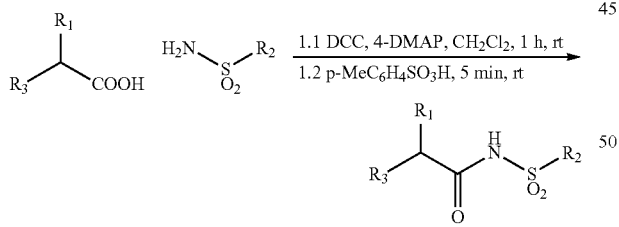

The reactions in Scheme 15 can be conducted according to methods described by Wang et al. [Tetrahedron Letters, 48(30), 5181-5184; 2007].

Scheme 16

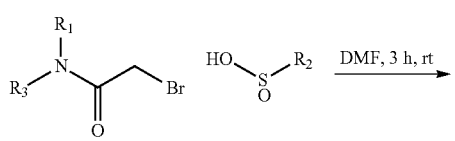

-continued

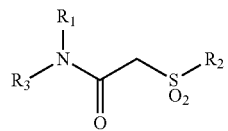

The reactions in Scheme 16 can be conducted according to methods described by Wang et al. [Chemical Communications, 47(40), 11336-11338; 2011]

Scheme 17

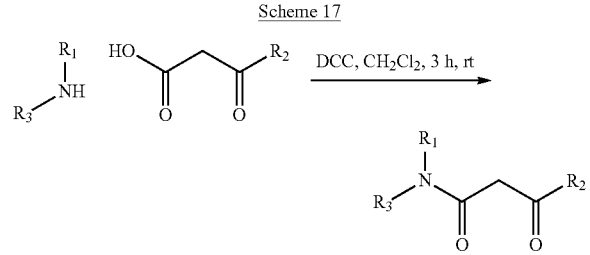

The reactions in Scheme 17 can be conducted according to methods described by Yuan et al. [Journal of Organic Chemistry, 78(11), 5385-5392; 2013].

Scheme 18

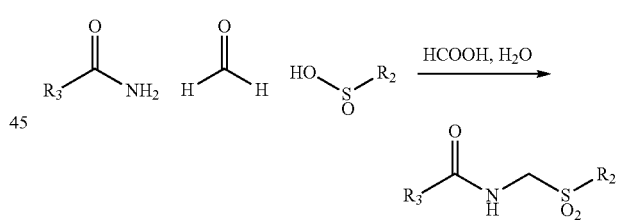

The reactions in Scheme 18 can be conducted according to methods described by Zyabrev et al. [Zhurnal Organicheskoi Khimii, 30(5), 715-19; 1994].

Scheme 19

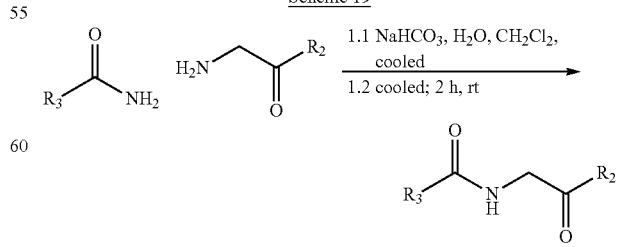

The reactions in Scheme 19 can be conducted according to methods described by Lakner, Frederick J. et al. [Synthesis, (12), 1987-1990; 2009].

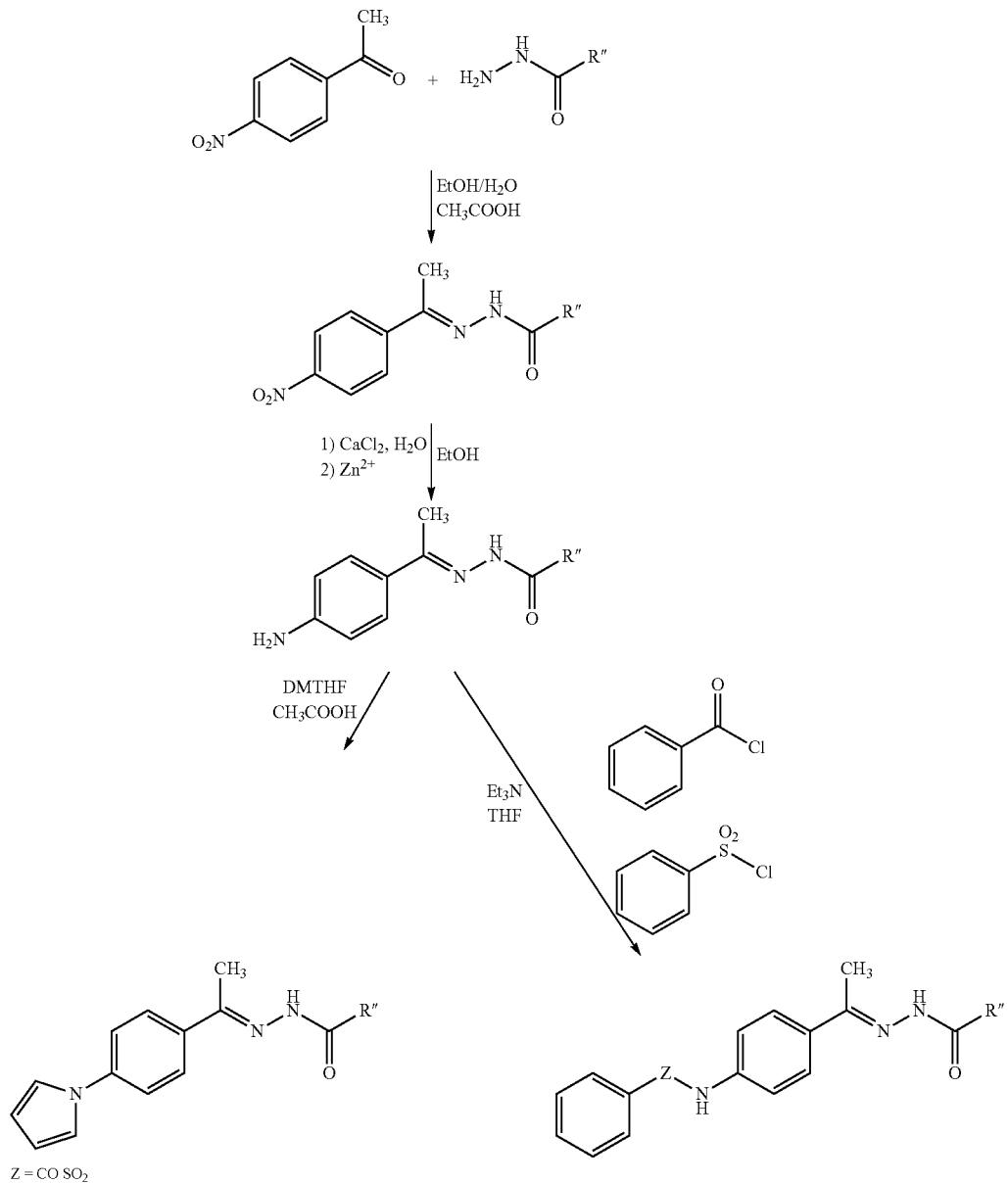

The reactions in Scheme 20 can be conducted according to well-known methods as set forth above.

Pharmaceutical Compositions

In a third aspect, the invention provides a pharmaceutical composition comprising a therapeutically effective amount of a polycyclic compound or a pharmaceutically acceptable salt, tautomer, or stereoisomer thereof;

wherein the polycyclic compound is of a formula selected from the group consisting of:

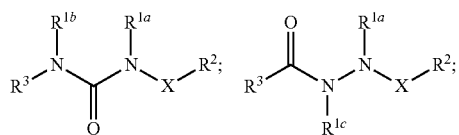

-continued

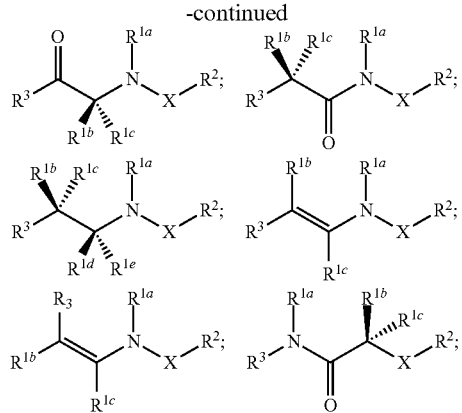

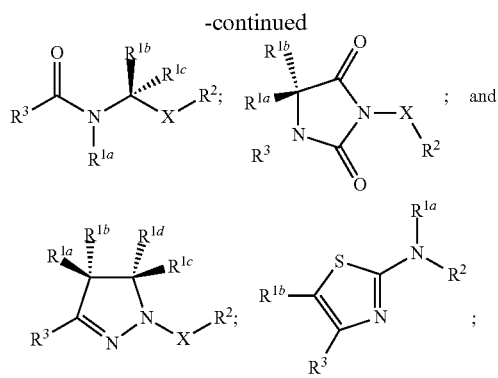

wherein:

X is a linking group selected from the group consisting of —S(O)$_2$— and —C(O)—;

$R^{1a}$, $R^{1b}$, $R^{1c}$, $R^{1d}$, and $R^{1e}$ are each independently selected from the group consisting of hydrogen, lower alkyl, fluoroalkyl, aryl, and heteroaryl; wherein the aryl or heteroaryl group has from 0 to 3 $R^4$ substituents;

$R^2$ is a first cyclic group selected from the group consisting of phenyl, naphthyl, and heteroaryl; wherein the $R^2$ group has from 0 to 3 $R^4$ substituents;

$R^3$ is a second cyclic group selected from the group consisting of phenyl, naphthyl, and heteroaryl; wherein the $R^3$ group has from 0 to 4 $R^4$ substituents;

each $R^4$ substituent is independently selected from the group consisting of $C_1$-$C_6$ alkyl, $C_2$-$C_6$ alkenyl, $C_2$-$C_6$ alkynyl, $C_1$-$C_6$ alkoxy, halo, —NO$_2$, —CF$_3$, —CN, —OR$^5$, —SR$^5$, —C(O)R$^5$, —NHC(O)R$^5$, —C(O)OR$^5$, —OC(O)R$^5$, —NR$^5$R$^6$, —C(O)NR$^5$R$^6$, —NHR$^5$C(O)NR$^6$R$^7$, —S(O)$_2$NR$^5$R$^6$, and a cyclic $R^4$ substituent; wherein the cyclic $R^4$ substituent is selected from the group consisting of aryl, heteroaryl, arylalkyl, heteroarylalkyl, cycloalkyl, cycloalkylalkyl, and heterocyclyl; and wherein the cyclic $R^4$ substituent has from 0 to 3 $R^8$ substituents;

each $R^5$, $R^6$, or $R^7$ is independently H, $C_1$-$C_6$ alkyl, $C_2$-$C_6$ alkenyl, $C_2$-$C_6$ alkynyl, $C_1$-$C_6$ alkoxy, halo, or a cyclic $R^5$ substituent; wherein the cyclic $R^5$ substituent is selected from the group consisting of aryl, heteroaryl, arylalkyl, heteroarylalkyl, cycloalkyl, cycloalkylalkyl, and heterocyclyl; and wherein the cyclic $R^5$ substituent has from 0 to 3 $R^8$ substituents; and each $R^8$ is independently $C_1$-$C_6$ alkyl, $C_2$-$C_6$ alkenyl, $C_2$-$C_6$ alkynyl, $C_1$-$C_6$ alkoxy, halo, aryl, heteroaryl, arylalkyl, heteroarylalkyl, cycloalkyl, cycloalkylalkyl, or heterocyclyl; and wherein adjacent $R^4$, $R^5$, $R^6$, or $R^7$ substituents may optionally join to form an additional fused ring selected from the group consisting of aryl, heteroaryl, cycloalkyl, and heterocyclyl; wherein the additional fused ring has from 0 to 3 $R^8$ substituents.

The compounds described herein can be used as pharmaceutical compositions comprising the compounds, together with one or more pharmaceutically acceptable excipients or vehicles, and optionally other therapeutic and/or prophylactic ingredients. Such excipients include liquids such as water, saline, glycerol, polyethyleneglycol, hyaluronic acid, ethanol, cyclodextrins, modified cyclodextrins (i.e., sufobutyl ether cyclodextrins) etc. Suitable excipients for non-liquid formulations are also known to those of skill in the art. Pharmaceutically acceptable salts can be used in the compositions of the present invention and include, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients and salts is available in *Remington's Pharmaceutical Sciences*, 18th Edition (Easton, Pa.: Mack Publishing Company, 1990).

Additionally, auxiliary substances, such as wetting or emulsifying agents, biological buffering substances, surfactants, and the like, may be present in such vehicles. A biological buffer can be virtually any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, may include other pharmaceutical agents, adjuvants, diluents, buffers, etc.

The invention includes a pharmaceutical composition comprising a compound of the present invention including isomers, tautomers, racemic or non-racemic mixtures of isomers, or pharmaceutically acceptable salts or solvates thereof together with one or more pharmaceutically acceptable carriers, and optionally other therapeutic and/or prophylactic ingredients.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents, tonicifying agents, and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, referenced above.

For oral administration, the composition will generally take the form of a tablet, capsule, a softgel capsule or may be an aqueous or nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

A pharmaceutically or therapeutically effective amount of the composition will be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the effective amount for a given situation can be determined by routine experimentation. The subject may be administered as many doses as is required to reduce and/or alleviate the signs, symptoms, or causes of the disorder in question, or bring about any other desired alteration of a biological system.

In some aspects, the invention presents the use of a compound of any of the aspects or embodiments disclosed herein in a method of any of the aspects or embodiments disclosed herein. In some aspects, the invention presents the use of a compound of any of the aspects or embodiments disclosed herein in the manufacture of a medicament for use in a method of any of the aspects and embodiments disclosed herein.

illustration; it is not intended to be exhaustive or to limit the invention to the precise forms disclosed. Persons skilled in the relevant art can appreciate that many modifications and variations are possible in light of the above teachings. It should be noted that the language used in the specification has been principally selected for readability and instructional purposes, and it may not have been selected to delineate or circumscribe the inventive subject matter. Accordingly, the disclosure of the aspects of the invention is intended to be illustrative, but not limiting, of the scope of the invention.

All references, issued patents, and patent applications cited within the body of the specification are hereby incorporated by reference in their entirety, for all purposes except insofar as their disclosure contradicts the express disclosure herein.

EXAMPLES

Example 1

General Procedure for the Synthesis of Benzhydrazide Derivatives: Representative Procedure for 2,4-Dimethylbenzohydrazide The materials were purchased from commercial supplies and were used without any additional purification.

All reactions were monitored by thin layer chromatography (TLC) on Silica gel 60 F254 plates. The plates were then observed using UV light (365 nm and 254 nm) with tool ENF 260 C/ F UV.

The silica gel (230-400 mesh) for column chromatography was purchased from Merck. The concentration of the solutions and/ or their evaporation has required the use of a rotatory evaporator (Buchi Rotavapor), operating at reduced pressure. The organic solutions were dried over anhydrous sodium sulphate (Merck).

Melting points were taken in open capillary tubes and are uncorrected. $^1$H NMR were recorded on a Bruker 300 MHz spectrometer in CDC13 or DMSO-d6 (with TMS for internal references). The chemical shifts are reported in units (ppm) relative to the internal reference tetramethylsilane (Me4Si).

All compounds were checked by TLC and $^1$H-NMR. The NMR data are consistent with the structures shown.

Step 1: 2,4-dimethyl benzoic acid (9g, 59.9 mmol) was dissolved in EtOH (150 ml), then $H_2SO_4$ (6 ml catalysis) was added. The solution was refluxed for 12 hours. After cooling the solvent was evaporated in vacuo. Water was added and the aqueous layer was back-extracted with ethyl acetate. The combined organic extracts were first washed with saturated sodium bicarbonate and then with brine, finally dried over $Na_2SO_4$, filtered through cotton and concentrated in vacuo. The crude product was purified by chromatography using Silica gel as stationary phase and a mixture EtOAc/CHCl$_3$ (1/1) as mobile phase to give 6.75 g of pure product as white crystals. Yield: 65%

Step 2: Ethyl 2,4-dimethyl benzoate (6.75 g, 38 mmol) was dissolved in hydrazine hydrate (78 ml, 80.26 g, 2.50 mol) and refluxed for 4 hours. After cooling the solvent was evaporated in vacuo. Water was added and the aqueous layer was back-extracted with ethyl acetate. The combined organic extracts were first washed with saturated sodium bicarbonate and then with brine, finally dried over $Na_2SO_4$, filtered through cotton and concentrated in vacuo. The crude product was purified by crystallization in EtOH to give 4.3 g of pure product as white crystals (68% yield).

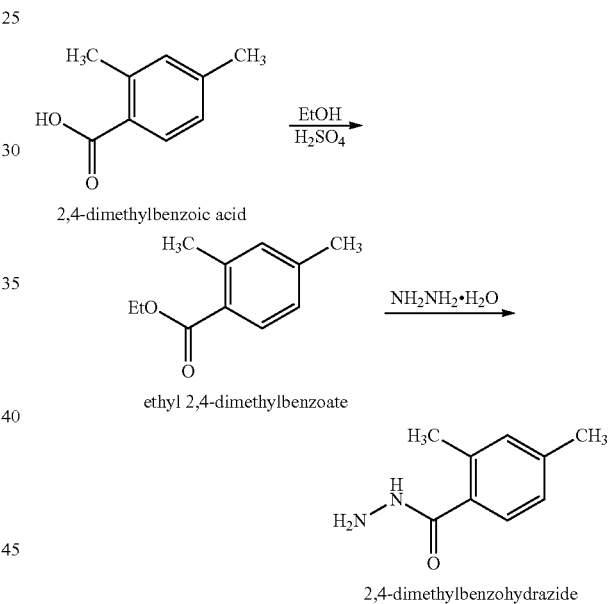

He, Lingyan et al. *J. Med. Chem.* 2009, 52(8), 2465-2481.

Example 2

General Procedure for the Synthesis of Benzhydrazones Derivatives

Representative procedure for N'-(1-(10H-phenothiazin-2-yl)ethylidene)-2,4-dimethylbenzohydrazide In a round bottom flask 2,4-dimethylbenzohydrazide (1 g, 6.1 mmol) was suspended in EtOH (80 ml) and 1-(10H-phenothiazin-2-yl)ethanone (1.47 g, 6.1 mmol) was added. The mixture was refluxed for 48 hours. On heating, pale yellow crystals were formed, filtered off, washed with EtOH and Et$_2$O and recrystallized from EtOH to give 1.2 g of pure product as brownish crystals. Yield: 51%.

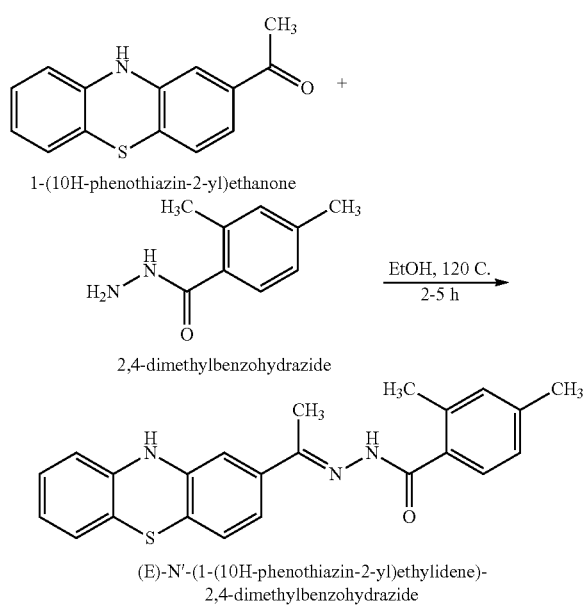

Zaky, R. R et al. *Spectrochimica Acta Part A: Molecular and Biomolecular Spectroscopy* 81, 28-34 (2011)

Example 3

Highly Effective Ubiquitin-Competing Molecules that Promote Frataxin Accumulation and Rescue the Aconitase Defect in Friedreich Ataxia Cells

METHODS

Cell culture and transfections. Human embryonic kidney HEK-293 cells were cultured in Dulbecco's modified Eagle's medium (DMEM) supplemented with 10% fetal bovine serum (FBS). HEK-293 cells were transfected using Lipofectamine 2000 reagents (Invitrogen), according to the manufacturer's instructions. Cells were plated on 6 cm dishes and transfected with 8 µg of total DNA (4 µg of pIRES-frataxin and 4 µg of HA-Ub). The day after transfection, cells were treated for 24 h with 10 µM UCM together with 10 µM proteasome inhibitor MG132 and 50 ng/ml deubiquitinating enzyme (DUB) inhibitor Ub-aldehyde. HEK-293 Flp-In cells (Invitrogen) are HEK-293 variants allowing the stable and isogenic integration and expression of a transfected gene. The HEK-293 clones stably expressing frataxin$^{1-210}$ or frataxin$^{K147R}$ were previously described (Condo et al., 2007; Rufini et al., 2011). FRDA 214 (GM16214) and FRDA 798 (GM16798) lymphoblasts, from clinically affected FRDA patients, as well as FRDA 215 (GM16215) and FRDA 241 (GM16241) lymphoblasts, from the correspondent heterozygous clinically unaffected sibling, were obtained from Coriell Cell Repositories (Camden, N.J., USA) and were cultured in RPMI supplemented with 15% FBS.

Antibodies. The following antibodies were used for Western Blot analysis: mAb anti-frataxin (MAB-10876, Immunological Sciences), mAb anti-tubulin (Sigma-Aldrich) and secondary antibody horseradish peroxidase-conjugated goat anti-mouse (Pierce).

Chemicals. Proteasome inhibitors: MG132 (Sigma-Aldrich); DUB inhibitors: Ub-aldehyde (Biomol) and N-ethylmaleimide (NEM; Sigma-Aldrich). Ubiquitin-competing molecules were obtained from Enamine or were synthesized. The identity and purity of the compounds obtained were determined by TLC analysis and $^1$H-NMR.

DNA constructs. The pIRES2-frataxin$^{1-210}$ and pIRES2-frataxin$^{K147R}$ constructs were previously described (Condò et al., 2006; Rufini et al., 2011). The HA-Ub construct was generated by M. Treier in Dirk Bohmann's lab (Treier et al., 1994).

Immunoblotting. Total cell extracts were prepared in IP buffer (50 mM Tris-HCl, pH 7.5, 150 mM NaCl, 1% Nonidet P-40, 5 mM EDTA, 5 mM EGTA) supplemented with Complete protease inhibitor cocktail (Roche Diagnostics). For in vivo detection of ubiquitin conjugates, 10 µM MG132, 50 ng/ml Ub-aldehyde and 2 mM NEM were added to the lysis buffer. Protein extract (50 µg) was separated by 12% SDS-PAGE, blotted onto a nitrocellulose membrane and detected with specific antibodies. The immunoreactive bands were detected by ECL (GE Healthcare) and imaged with a ChemiDoc XRS system (Bio-Rad Laboratories). Densitometric analysis was performed using the ImageLab 4.1 Software (Bio-Rad Laboratories).

Steady-state fluorescence measurements. Human recombinant frataxin precursor (aa 1-210) was expressed and purified by GenScript Corp., N.J., USA. Steady-state fluorescence spectra were recorded at 20° C. using an ISS PC1 fluorometer (Iss Inc, Champain, Ill. Usa). The affinity of frataxin for the ligands studied in this paper was determined by monitoring the decrease in Trp fluorescence upon the addition of these molecules to solutions. The concentration of the protein was 2 µM while the concentration of the ligands varied from 0.5 to 25 µM. At the excitation wavelength of 280 nm, emission spectra were recorded between 290 and 440 nm, using a 4×4 mm path-length quartz fluorescence microcuvette (Hellma GmbH & Co., Müllheim/Baden, Germany). The spectra were corrected using an instrument correction curve obtained with standard fluorescent compounds such as N-acetyl tryptophanamide (NATA). All measurements were also corrected for the inner-filter effect. To simulate the absorption of ligand molecules at the excitation and the emission wavelengths, two cuvettes (2 mm optical length), containing a solution of ligands in buffer, were placed along the excitation and emission pathways. The fluorescence of NATA was thus measured varying the concentration of quencher and four correction curves (one for each ligand) were obtained.

Data were then plotted as fractional loss of Trp fluorescence (ΔF/F0) versus ligand concentration. Experimental data were analyzed by nonlinear regression through a hyperbolic binding isotherm, using the Kaleidagraph program (Synergy Software).

Enzyme assays. For determinations of aconitases and citrate synthase activity, FRDA lymphoblasts were washed twice with ice-cold Dulbecco's Phosphate Buffered Saline (DPBS) and lysed in CelLytic M buffer (Sigma-Aldrich) supplemented with Complete protease inhibitor cocktail EDTA-free (Roche) and 2 mM trisodium citrate. Citrate was included to prevent the inactivation of iron-sulfur cluster of aconitases. Total aconitase activity was measured spectrophotometrically at 340 nm using the BIOXYTECH Aconitase-340™ Assay (OxisResearch™ 21041). The assay reactions, containing 150 µg of cell extract, were performed following the supplier's procedure, with the exception of temperature incubation at 25° C. Citrate synthase activity was assessed using 15 µg of cell extract with the Citrate Synthase Assay Kit (Sigma-Aldrich CS0720).

The aconitase activities were normalized with respect to citrate synthase ratios; one milliunit of enzyme was defined as the amount of protein that converted 1 nmol of $NADP^+$ in 1 min at 25° C.

RESULTS

Computational screening for ubiquitin-competing molecules (UCMs). In order to design small molecules able to inhibit the ubiquitination of frataxin, an extended analysis of frataxin accessible surfaces has been performed, extending our previous work, by taking into account protein flexibility. This analysis allowed us to identify more druggable binding pockets on frataxin. By focusing our analysis on the areas more proximal to K147, and by using virtual screening of commercially available compound libraries, about a thousand compounds were docked on available NMR and x-ray structures of human frataxin. These molecules were predicted to interact with frataxin near to K147 (FIGS. 1A-1D).

FIGS. 1A-1D show a model of UCM71 docking to frataxin. The crystal structure of frataxin (gray cartoon) with solvent accessible molecular surface around the W155 pocket is shown in FIG. 1A. Overall structure as grey cartoon, molecular surface colored by lipophilicity (hydrophilic in magenta, lipophilic in green).

Figure 1B:
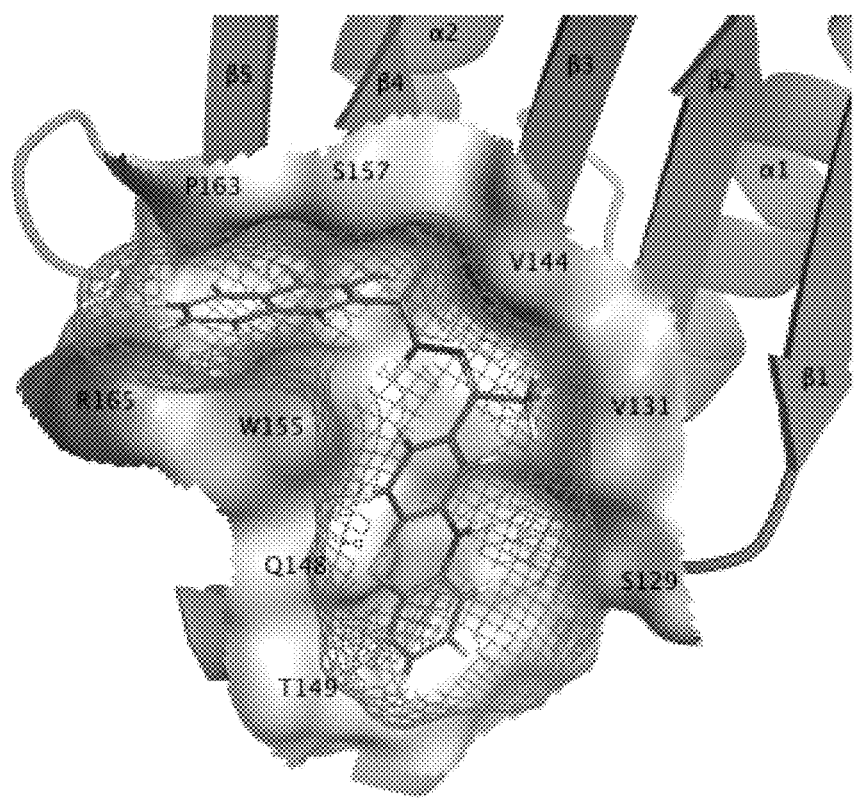

FIG. 1B shows the W155 pocket with the ligand UCM71 (ball and stick, CPK colors): the solvent accessible ligand surface (light blue mesh) fits perfectly with the naphtyl moiety buried by W155, P163, and 5157. The phenothiazine ring recognizes the flat region formed by N146 and K147 (label not shown for clarity) and delimited by side chains of V131, 5129, T149, and Q148.

Figure 1C:
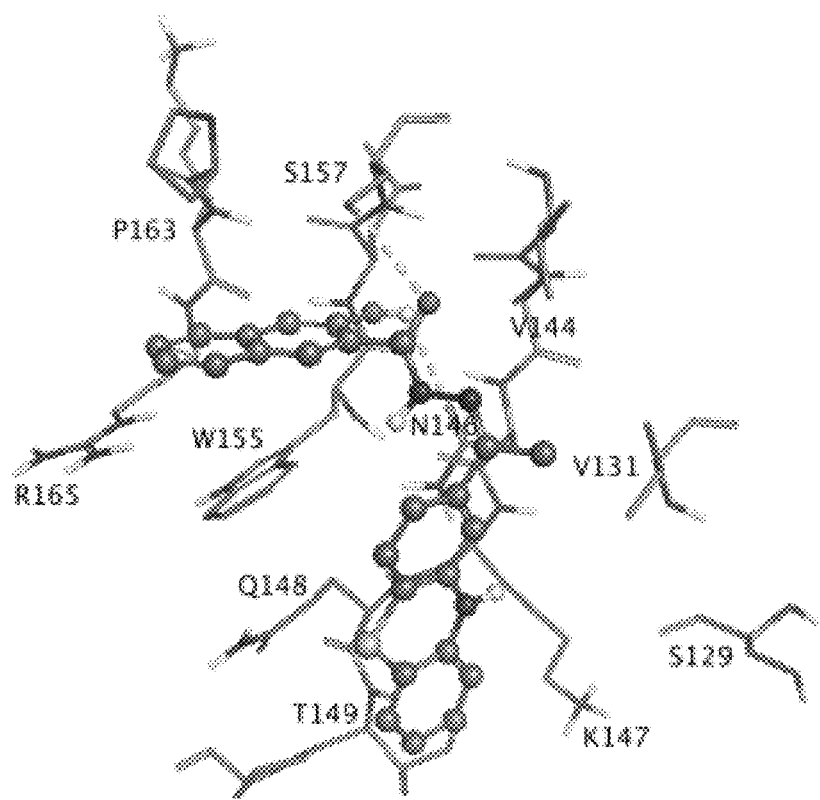

FIG. 1C shows selected interactions of UCM71 with frataxin. Hydrogen bonds are formed between the hydroxyl substituent of the naphtyl group and the side chain of N146 and between the carbonyl group of the carbonyl-hydrazone scaffold and the hydroxyl of S157. These interactions induce minor rearrangements in the involved side-chains of N146 (flip of terminal amide) and S157.

Figure 1D:
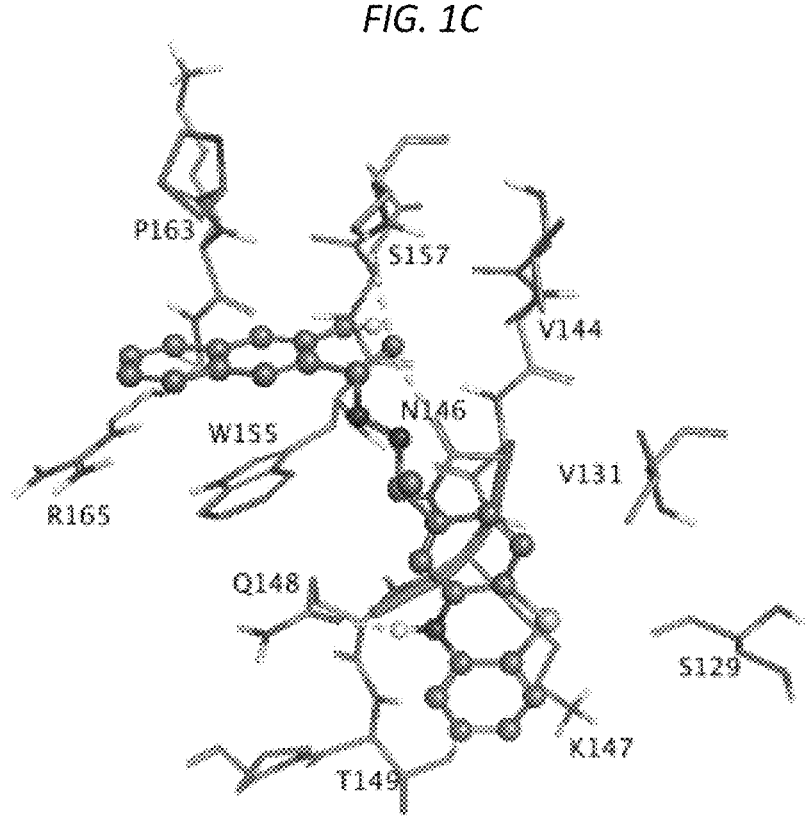

As shown in FIG. 1D, the flexibility of the carbonyl-hydrazone scaffold permits the flip of phenothiazine moiety to points its central amino group toward Q148 inducing the flip of the amide group of its side chain resulting in the formation of a strong hydrogen bond.

Promising candidates were subjected to functional validation.

UCMs increase frataxin levels. To validate UCM activity, UCMs were tested their effect in human HEK-293 cells stably expressing single copy frataxin (293-frataxin). These cells allow the detection of all forms of frataxin, including the frataxin precursor. Compounds that were able to enhance frataxin precursor levels were synthesized, further chemically modified according to the docking model and tested again in 293-frataxin. Approximately 200 new candidate UCMs were tested in functional assays. Through this iterative process, new UCMs that promote frataxin precursor with surprising efficiency were identified. Indeed, treatment of 293-frataxin cells with 10 μM UCM53, UCM108 and UCM71 is able to induce frataxin precursor accumulation (FIG. 2A) more efficiently than the previously described UCM2, (referred to as NSC620301 in (Rufini et al., 2011)) or with the proteasome inihibitor MG132. Importantly, an accumulation of mature frataxin can also be observed in these cells when treatment is prolonged for 3 days (FIG. 2B).

Figure 2A:
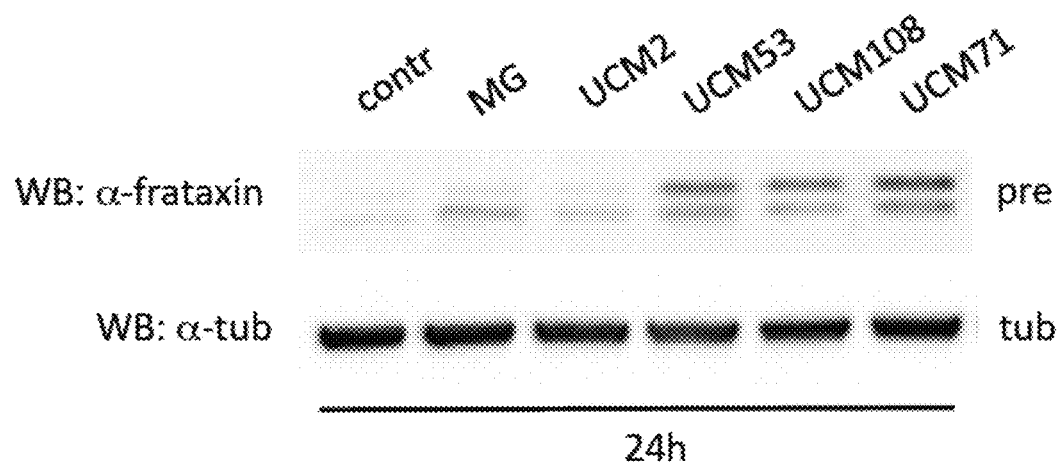
FIGS. 2A-2B illustrate that ubiquitin-competing molecules (UCMs) increase frataxin levels. Treatment of 293-frataxin cells with 10 µM UCM53, UCM108 and UCM71 is able to induce frataxin precursor accumulation (FIG. 2A) and, after 3 days, the accumulation of mature frataxin (FIG. 2B).

Detection of frataxin precursor accumulation is shown in FIG. 2A. 293 Flp-In cells stably expressing frataxin$^{1-210}$ were treated for 24 hrs with 10 μM of the indicated UCM or 10 μM MG132 (MG). Total cell extracts were resolved on SDS-PAGE and analyzed with anti-frataxin antibody, or anti-tubulin, as a loading control. Pre: precursor; tub: tubulin.

Figure 2B:
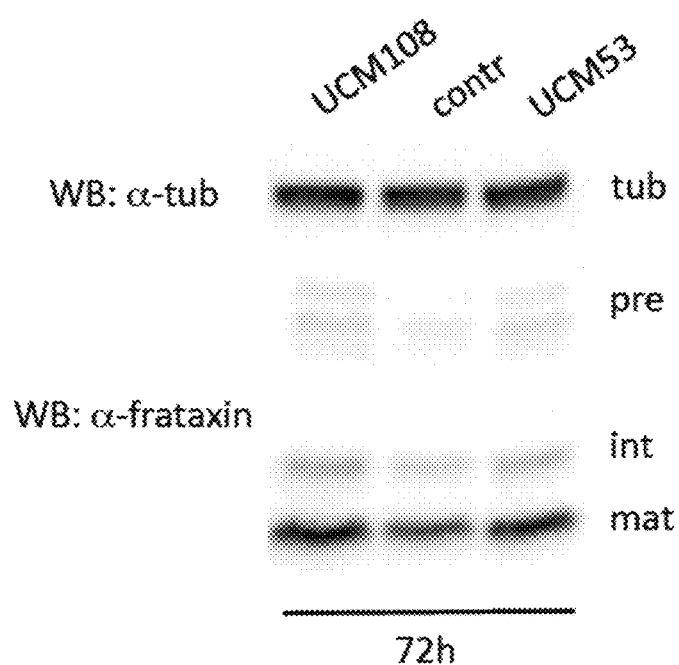

Detection of mature frataxin accumulation is shown in FIG. 2B. 293 Flp-In cells stably expressing frataxin$^{1-210}$ were treated for 72 hrs with 10 μM of the indicated UCM. Total cell extracts were resolved on SDS-PAGE and analyzed with anti-frataxin antibody, or anti-tubulin, as a loading control. Pre: precursor, int: intermediate, mat: mature; tub: tubulin.

Structures of the active compounds described in this study are shown in Table 3.

TABLE 3

Chemical structure of the active compounds described in the present study.

| Compound name | Structure |
|---|---|
| UCM53 | 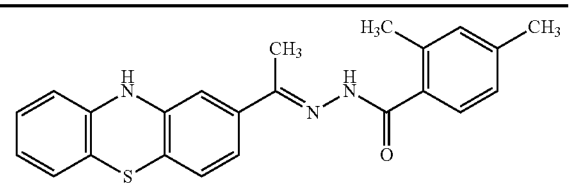 |
| UCM71 | 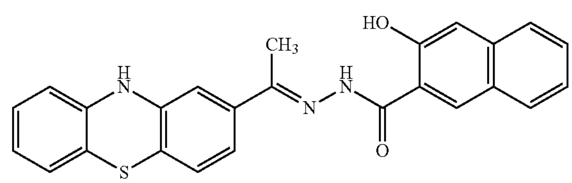 [SMILES: C/C(=N\NC(=O)c1cc2ccccc2cc1O)c1ccc2c(c1)Nc1ccccc1S2] |
| UCM108 | 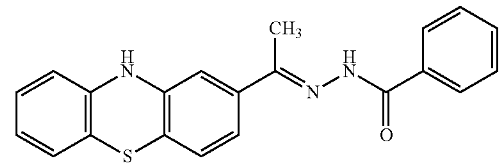 [SMILES: C/C(=N\NC(=O)c1ccccc1)c1ccc2c(c1)Nc1ccccc1S2] |

Figure 3A:
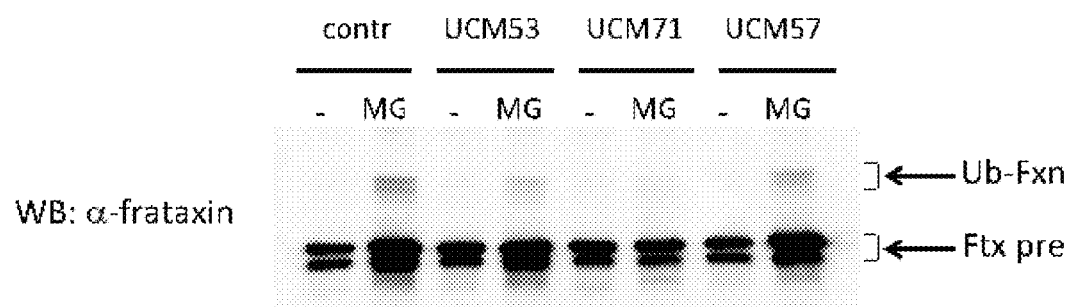
FIGS. 3A-3B illustrate that UCMs prevent frataxin ubiquitination.
Figure 3B:
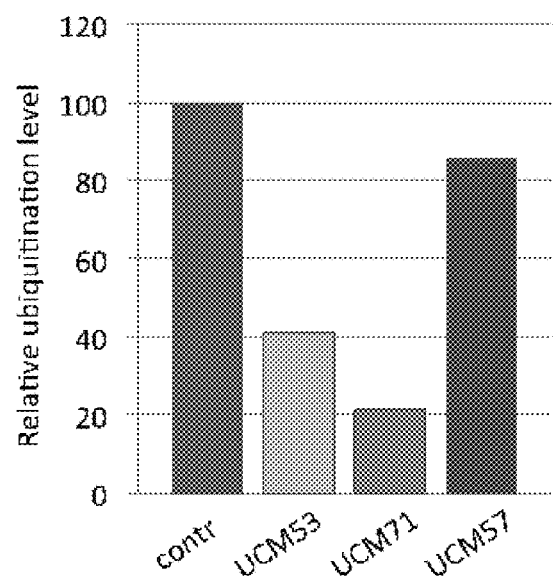

UCMs prevent frataxin ubiquitination. To test whether the new compounds promote frataxin accumulation by preventing its ubiquitin/proteasome-dependent degradation, their impact on frataxin ubiquitination was evaluated. To this aim, an in vivo ubiquitination assay was performed. HEK-293 cells were transiently co-transfected with HA-tagged-ubiquitin and frataxin, in the presence of proteasome inhibitor and deubiquitinase inhibitor to allow the accumulation of ubiquitinated species, in the presence of the selected compounds. The ubiquitination status of frataxin was evaluated by SDS-PAGE of total cell lysates and anti-frataxin immunoblotting. As previously described, in this experimental setting, frataxin monoubiquitinated forms can be detected by anti-frataxin antibody as a slower migrating band above frataxin precursor (Rufini et al., 2011). Ubiquitination level was measured as the ratio between the levels of ubiquitinated frataxin and frataxin precursor. As shown in FIGS. 3A-3B, UCM53 and UCM71 but not the control non-effective molecule UCM57, can significantly abrogate frataxin ubiquitination. These data suggest that the selected UCMs interfere with frataxin ubiquitination in living cells.

FIG. 3A shows SDS-PAGE analysis of cell extracts containing frataxin precursor and ubiquitin-conjugate frataxin. 293 cells were transiently co-transfected with HA-Ub and frataxin$^{1-210}$. 24 hours after transfection, cells were treated with 10 µM of the indicated UCM or with DMSO alone (contr). UCM57 was used as a non-effective control molecule. Cells were harvested 48 hours after transfection. Where indicated (MG), cells were also treated with 10 µM MG132 and 50 ng/ml ubiquitin-aldehyde for the last 16 hours. Total cell extracts were resolved on SDS-PAGE and revealed with anti-frataxin antibody. The arrows indicate the bands corresponding to frataxin precursor (Fxn-pre) and ubiquitin-conjugated frataxin (Ub-Fxn). Relative ubiquitination levels, quantitated as the densitometric ratio between ubiquitinated frataxin bands and frataxin precursor bands for each MG132-treated lanes, are plotted in FIG. 3B.

UCM promote frataxin accumulation by preventing K147-dependent degradation. K147 is the crucial ubiquitination site on frataxin, which was previously shown by this laboratory. Since these compounds are able to efficiently abrogate frataxin ubiquitination, they are believed to act by interfering with ubiquitination on K147. Thus, to validate this hypothesis, their effect on the frataxin mutant that lacks K147 was evaluated. This mutant cannot be ubiquitinated and is therefore resistant to UPS-mediated degradation. Small molecules that act by preventing ubiquitination on K147 are believed to be ineffective on this mutant. Therefore, their effect on HEK-293 cells stably expressing the ubiquitin-refractory frataxin$^{K147R}$ mutant (293-frataxin$^{K147R}$) was tested. Cells were treated for 24 hours with the indicated compounds and frataxin precursor levels analysed by western blot on total cell extract. Indeed, when 293-frataxin$^{K147R}$ are treated with the selected UCM, no significant increase in frataxin precursor levels could be detected (FIGS. 4A-4B), compared to what was observed in 293-frataxin, expressing wild-type frataxin. These data are consistent with UCM acting on frataxin by interfering with the K147-dependent degradation pathway.

Figure 4A:
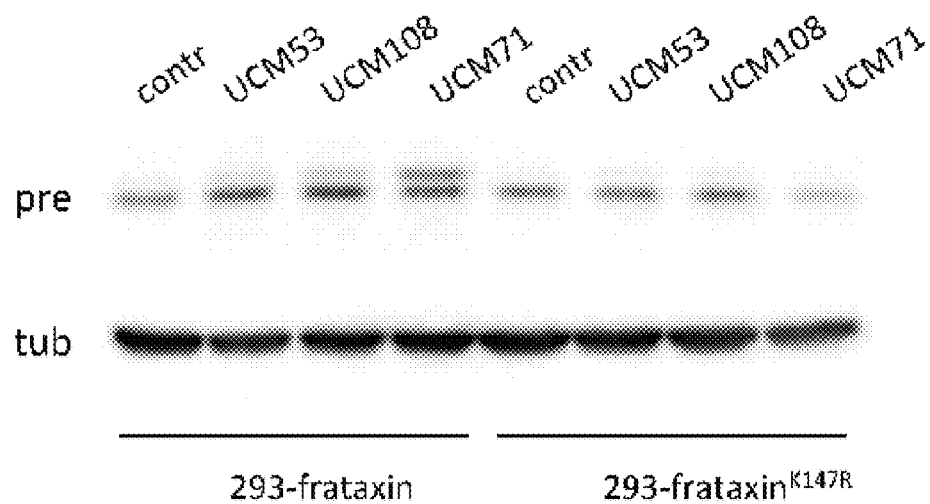
FIGS. 4A-4B illustrate that UCMs promote frataxin accumulation by preventing K147-dependent degradation.
Figure 4B:
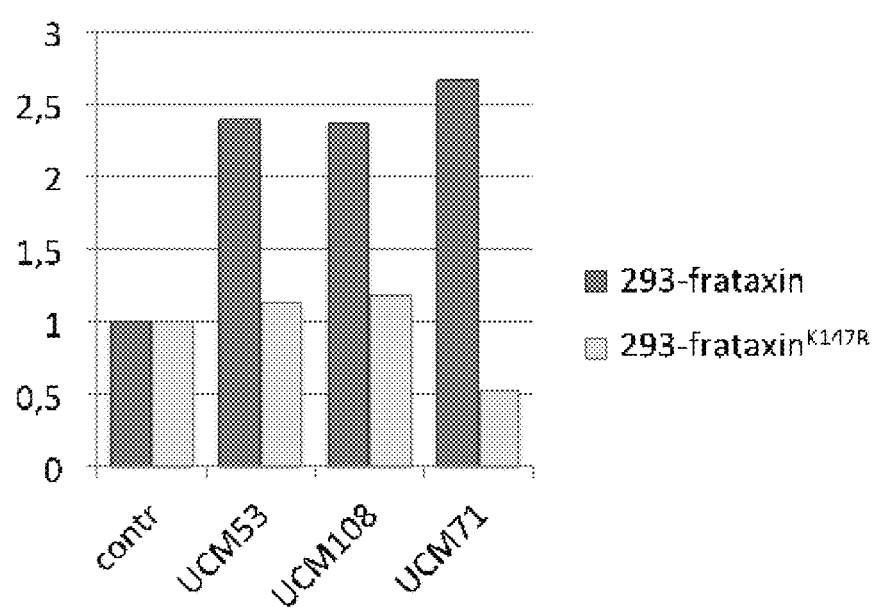

FIG. 4A shows the SDS-PAGE analysis of cell extracts containing frataxin precursor. 293 Flp-In cells stably expressing frataxin$^{1-21-}$ (293-frataxin) or the lysine-mutant frataxin$^{K147R}$ (293-frataxin$^{K147R}$) were treated for 24 hrs with 10 µM of the indicated UCM. Proteins were resolved on SDS-PAGE and revealed with anti-frataxin antibody or anti-tubulin, as a loading control. Pre: precursor; tub: tubulin. The relative frataxin precursor levels, as quantitated by densitometric analysis, are plotted in FIG. 4B.

UCMs interact with frataxin. Ubiquitin-competing molecules were selected through structure-based virtual screening for their potential ability to interact with frataxin on its ubiquitination site. Since they are in fact able to prevent frataxin ubiquitination and to interfere with its K147-dependent degradation, confirmation of their ability to physically interact with frataxin was sought. Therefore, the interaction propensities of frataxin with these molecules were investigated by fluorescence spectroscopy through the analysis of the changes of the signal of the protein tryptophan residues in the presence of the different compounds.

Figure 5:
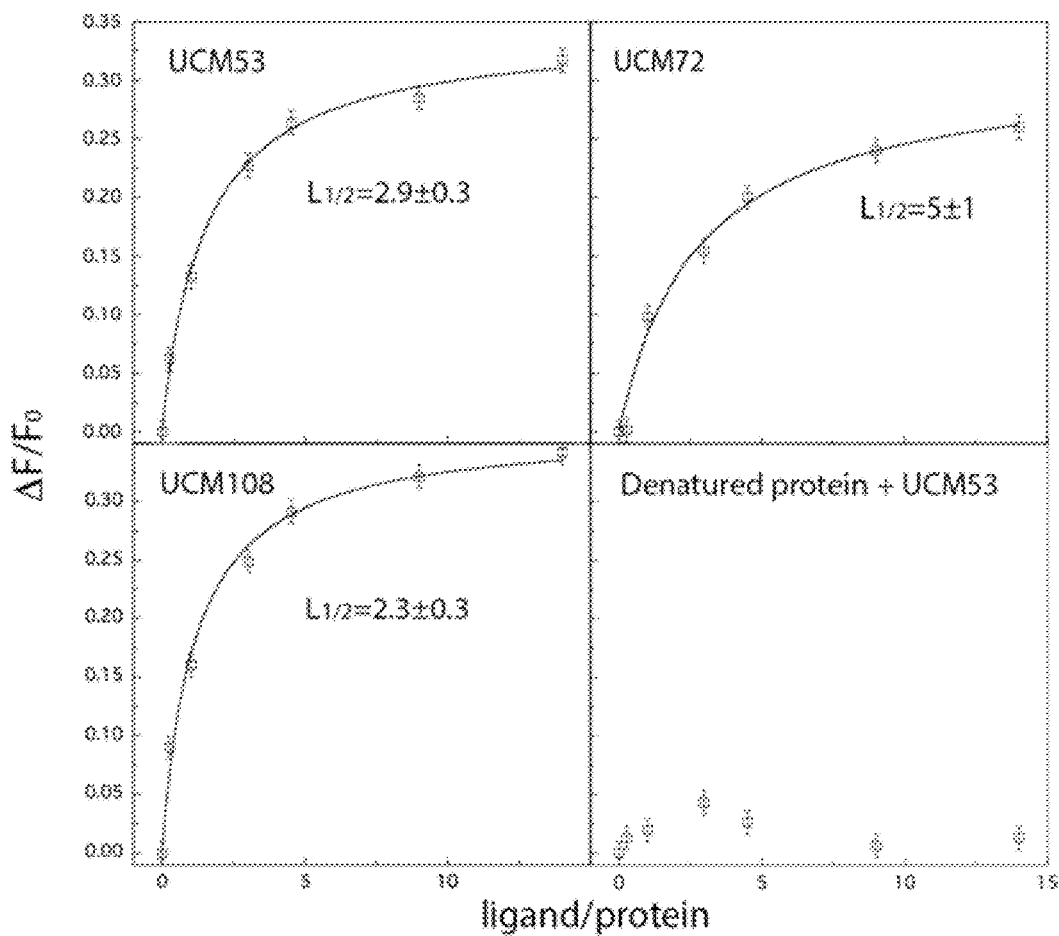
FIG. 5 illustrates that UCMs interact with frataxin.

FIG. 5 shows the binding isotherm of the protein to three different compounds, UCM53 and UCM108 that promote frataxin accumulation, and UCM72 that is unable to promote fataxin accumulation (see below), as a control. One of the effective compounds (UCM53) was also exposed to the denatured protein. The corresponding binding affinity constants ($L_{1/2}$) are reported in each panel. UCM53 and UCM108 showed strong fluorescence changes (left panels) and the lowest binding affinity constants, while the control UCM72 showed the highest binding affinity constant (upper right panel). Fluorescent changes induced by UCM53 were completely lost using the denatured protein (lower right panel). These results indicate that UCM53 and UCM108 strongly interact with tryptophans likely due to a quite efficient binding.

FIG. 5 shows fluorescence studies of the interaction of 2 µM recombinant frataxin precursor with different concentration of the indicated UCM (ligand). The graphs represent the fractional loss of the protein fluorescence intensity ($\Delta F/F_0$), in the presence of different concentration of ligand, versus the ratio between ligand and frataxin. The interaction with UCM53 was also analyzed in the case of frataxin precursor previously denatured in 3M guanidinium hydrochloride (lower right panel). The half-saturation binding constant, $L_{1/2}$ (µM), of frataxin precursor with different UCM is indicated in each panel.

Figure 6A:
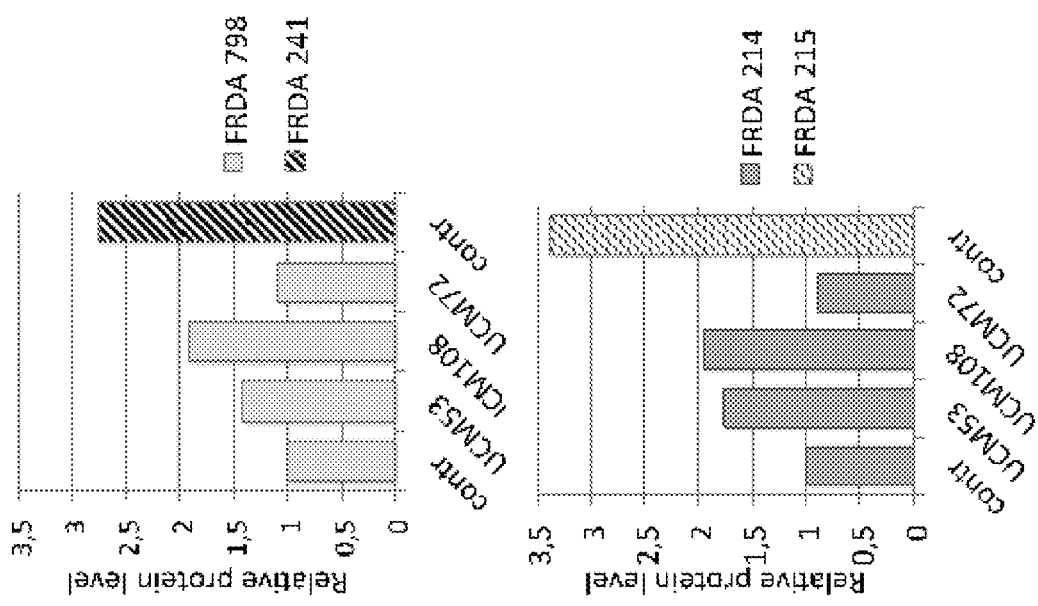
FIGS. 6A-6C illustrate that UCMs promote frataxin accumulation in FRDA cells and rescue the aconitase defect.
Figure 6A:
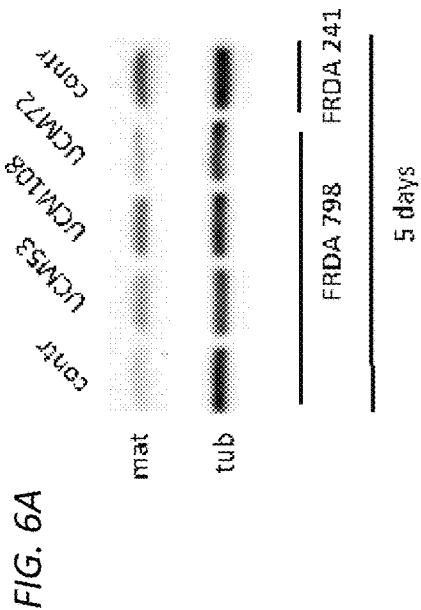
Figure 6B:
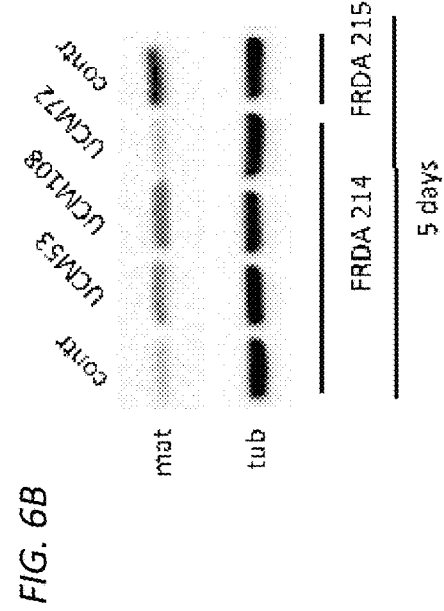

UCM compounds promote frataxin accumulation in FRDA cells and rescue the aconitase defect. The efficacy of the UCM compounds was tested in FRDA patients-derived cells (FIGS. 6A-6B). Lymphoblast cell lines derived from two different patients, FRDA 798 and FRDA 214 were cultured for 5 days in the presence of 10 µM of UCM53 or UCM108. UCM71 could not be evaluated because of its toxicity over a long-term treatment. Frataxin levels were quantitated by western blot analysis on whole cell extracts using anti-frataxin antibody, or anti-tubulin, as a loading control. The relative frataxin abundance was quantitated by densitometric analysis and normalized with tubulin levels. One representative experiment out of five performed with similar results is shown. Tub: tubulin; mat: mature frataxin.

Importantly, a significant accumulation of mature frataxin was observed when cells were cultured in the presence of UCM53 or UCM108, compared to cells treated with vehicle alone (control), or UCM72. Frataxin levels in treated cells derived from patients are also compared to the levels observed in cells derived from unaffected carrier siblings (FRDA 241 and FRDA 215).

Figure 6C:
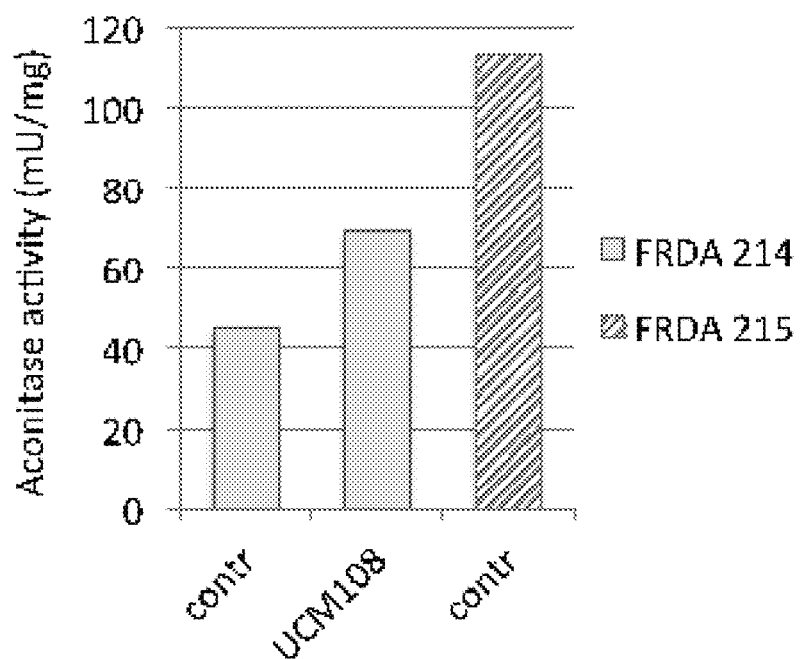

Moreover, to validate a functional recovery of frataxin levels, rescue of cellular aconitases activity was evaluated in FRDA cells upon treatment with UCMs. A significant increase in aconitases activity was observed in patient-derived lymphoblast cell line FRDA 214 after treatment with UCM108 for 5 days (FIG. 6C). Aconitases activity in cells derived from an unaffected carrier sibling (FRDA 215) is also shown for comparison. Thus, importantly, these data indicate that treatment with UCMs allows accumulation of a functional form of mature frataxin with consequent reactivation of ISC biogenesis.

Figure 7:
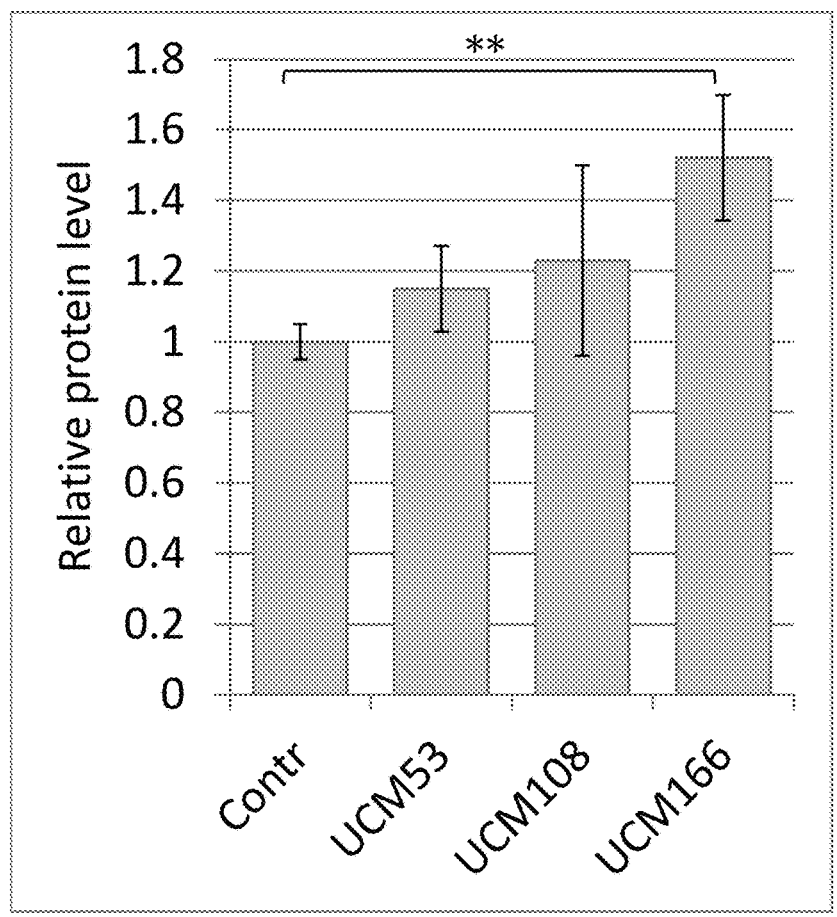
FIG. 7 illustrates that the compound UCM 166 promotes frataxin accumulation in FRDA cells.

UCM166 efficiently promotes frataxin accumulation in FRDA cells. The efficacy of a specific compound, UCM166, was tested in FRDA patients-derived cells. (The structure of UCM166 is as shown previously.) FRDA patient-derived lymphoblast cell line FRDA 203 was cultured in the presence of 1 µM of UCM166 or DMSO alone (as a control) for 4 days. Total cell extracts were resolved on SDS-PAGE and analyzed in a western blot with anti-frataxin antibody, or anti-tubulin, as a loading control. FIG. 7 represents the relative frataxin abundance as quantified by densitometric analysis and normalized with tubulin levels. The data represent the mean±S.E.M. from five different independent experiments. P-value was calculated with Student's t-test and was statistically significant (**P<0.05) compared to non-treated conditions.

REFERENCES

1. Pandolfo, M. & Pastore, A. The pathogenesis of Friedreich ataxia and the structure and function of frataxin. *J Neurol* 256 Suppl 1, 9-17 (2009).
2. Pandolfo, M. Friedreich ataxia: the clinical picture. *J Neurol* 256 Suppl 1, 3-8 (2009).
3. Puccio, H. Multicellular models of Friedreich ataxia. *J Neurol* 256 Suppl 1, 18-24 (2009).
4. Condò, I., et al. In vivo maturation of human frataxin. *Hum Mol Genet* 16, 1534-1540 (2007).
5. Schmucker, S., Argentini, M., Carelle-Calmels, N., Martelli, A. & Puccio, H. The in vivo mitochondrial two-step maturation of human frataxin. *Hum Mol Genet* 17, 3521-3531 (2008).
6. Acquaviva, F., et al. Extra-mitochondrial localisation of frataxin and its association with IscU1 during enterocyte-like differentiation of the human colon adenocarcinoma cell line Caco-2. *J Cell Sci* 118, 3917-3924 (2005).
7. Condò, I., Ventura, N., Malisan, F., Tomassini, B. & Testi, R. A pool of extramitochondrial frataxin that promotes cell survival. *J Biol Chem* 281, 16750-16756 (2006).
8. Condò, I., et al. Molecular control of the cytosolic aconitase/IRP1 switch by extramitochondrial frataxin. *Hum Mol Genet* doi:10.1093/hmg/ddp592(2010).
9. Yoon, T. & Cowan, J. A. Iron-sulfur cluster biosynthesis. Characterization of frataxin as an iron donor for assembly of [2Fe-2S] clusters in ISU-type proteins. *J Am Chem Soc* 125, 6078-6084 (2003).
10. Bulteau, A. L., et al. Frataxin acts as an iron chaperone protein to modulate mitochondrial aconitase activity. *Science* 305, 242-245 (2004).
11. Adinolfi, S., et al. Bacterial frataxin CyaY is the gatekeeper of iron-sulfur cluster formation catalyzed by IscS. *Nat Struct Mol Biol* 16, 390-396 (2009).
12. Delatycki, M. B. Evaluating the progression of Friedreich ataxia and its treatment. *J Neurol* 256 Suppl 1, 36-41 (2009).
13. Schulz, J. B., Di Prospero, N. A. & Fischbeck, K. Clinical experience with high-dose idebenone in Friedreich ataxia. *J Neurol* 256 Suppl 1, 42-45 (2009).
14. Tsou, A. Y., Friedman, L. S., Wilson, R. B. & Lynch, D. R. Pharmacotherapy for Friedreich ataxia. *CNS Drugs* 23, 213-223 (2009).
15. Gottesfeld, J. M. Small molecules affecting transcription in Friedreich ataxia. *Pharmacol Ther* 116, 236-248 (2007).
16. Marmolino, D. & Acquaviva, F. Friedreich's Ataxia: from the (GAA)n repeat mediated silencing to new promising molecules for therapy. *Cerebellum* 8, 245-259 (2009).
17. Schwartz, A. L. & Ciechanover, A. Targeting proteins for destruction by the ubiquitin system: implications for human pathobiology. *Annu Rev Pharmacol Toxicol* 49, 73-96 (2009).
18. Treier, M., Staszewski, L. M. & Bohmann, D. Ubiquitin-dependent c-Jun degradation in vivo is mediated by the delta domain. *Cell* 78, 787-798 (1994).
19. Musco, G., et al. Towards a structural understanding of Friedreich's ataxia: the solution structure of frataxin. *Structure* 8, 695-707 (2000).
20. Dhe-Paganon, S., Shigeta, R., Chi, Y. I., Ristow, M. & Shoelson, S. E. Crystal structure of human frataxin. *J Biol Chem* 275, 30753-30756 (2000).
21. Brady, G. P., Jr. & Stouten, P. F. Fast prediction and visualization of protein binding pockets with PASS. *J Comput Aided Mol Des* 14, 383-401 (2000).
22. Trott, O. & Olson, A. J. AutoDock Vina: improving the speed and accuracy of docking with a new scoring function, efficient optimization, and multithreading. *J Comput Chem* 31, 455-461 (2010).
23. Irwin, J. J. & Shoichet, B. K. ZINC—a free database of commercially available compounds for virtual screening. *J Chem Inf Model* 45, 177-182 (2005).
24. Teague, S. J., Davis, A. M., Leeson, P. D. & Oprea, T. The Design of Leadlike Combinatorial Libraries. *Angew Chem Int Ed Engl* 38, 3743-3748 (1999).
25. Deshaies, R. J. & Joazeiro, C. A. RING domain E3 ubiquitin ligases. *Annu Rev Biochem* 78, 399-434 (2009).
26. Rotin, D. & Kumar, S. Physiological functions of the HECT family of ubiquitin ligases. *Nat Rev Mol Cell Biol* 10, 398-409 (2009).
27. Xu, P., et al. Quantitative proteomics reveals the function of unconventional ubiquitin chains in proteasomal degradation. *Cell* 137, 133-145 (2009).
28. Boutet, S. C., Disatnik, M. H., Chan, L. S., Iori, K. & Rando, T. A. Regulation of Pax3 by proteasomal degradation of monoubiquitinated protein in skeletal muscle progenitors. *Cell* 130, 349-362 (2007).
29. Kravtsova-Ivantsiv, Y., Cohen, S. & Ciechanover, A. Modification by single ubiquitin moieties rather than polyubiquitination is sufficient for proteasomal processing of the p105 NF-kappaB precursor. *Mol Cell* 33, 496-504 (2009).
30. Saeki, Y., et al. Lysine 63-linked polyubiquitin chain may serve as a targeting signal for the 26S proteasome. *EMBO J* 28, 359-371 (2009).
31. Iwai, K. & Tokunaga, F. Linear polyubiquitination: a new regulator of NF-kappaB activation. *EMBO Rep* 10, 706-713 (2009).
32. Komander, D. The emerging complexity of protein ubiquitination. *Biochem Soc Trans* 37, 937-953 (2009).
33. Yonashiro, R., et al. A novel mitochondrial ubiquitin ligase plays a critical role in mitochondrial dynamics. *EMBO J* 25, 3618-3626 (2006).
34. Li, W., et al. Genome-wide and functional annotation of human E3 ubiquitin ligases identifies MULAN, a mitochondrial E3 that regulates the organelle's dynamics and signaling. *PLoS One* 3, e1487 (2008).
35. Germain, D. Ubiquitin-dependent and -independent mitochondrial protein quality controls: implications in ageing and neurodegenerative diseases. *Mol Microbiol* 70, 1334-1341 (2008).

36. Wright, G., Terada, K., Yano, M., Sergeev, I. & Mori, M. Oxidative stress inhibits the mitochondrial import of preproteins and leads to their degradation. *Exp Cell Res* 263, 107-117 (2001).

37. Habelhah, H., et al. Regulation of 2-oxoglutarate (alpha-ketoglutarate) dehydrogenase stability by the RING finger ubiquitin ligase Siah. *J Biol Chem* 279, 53782-53788 (2004).

Al-Mandawi, S., Pinto, R. M., Ismail, O., Varshney, D., Lymperi, S., Sandi, C., Trabzuni, D., and Pook, M. (2008). The Friedreich ataxia GAA repeat expansion mutation induces comparable epigenetic changes in human and transgenic mouse brain and heart tissues. Hum Mol Genet 17, 735-746.

Bedford, L., Lowe, J., Dick, L. R., Mayer, R. J., and Brownell, J. E. (2011). Ubiquitin-like protein conjugation and the ubiquitin-proteasome system as drug targets. Nature reviews Drug discovery 10, 29-46.

Bidichandani, S. I., Ashizawa, T., and Patel, P. I. (1998). The GAA triplet-repeat expansion in Friedreich ataxia interferes with transcription and may be associated with an unusual DNA structure. Am J Hum Genet 62, 111-121.

Brownell, J. E., Sintchak, M. D., Gavin, J. M., Liao, H., Bruzzese, F. J., Bump, N. J., Soucy, T. A., Milhollen, M. A., Yang, X., Burkhardt, A. L., et al. (2010). Substrate-assisted inhibition of ubiquitin-like protein-activating enzymes: the NEDD8 E1 inhibitor MLN4924 forms a NEDD8-AMP mimetic in situ. Molecular cell 37, 102-111.

Bulteau, A. L., O'Neill, H. A., Kennedy, M. C., Ikeda-Saito, M., Isaya, G., and Szweda, L. I. (2004). Frataxin acts as an iron chaperone protein to modulate mitochondrial aconitase activity. Science 305, 242-245.

Campuzano, V., Montermini, L., Molto, M. D., Pianese, L., Cossee, M., Cavalcanti, F., Monros, E., Rodius, F., Duclos, F., Monticelli, A., et al. (1996). Friedreich's ataxia: autosomal recessive disease caused by an intronic GAA triplet repeat expansion. Science 271, 1423-1427.

Chen, Q., Xie, W., Kuhn, D. J., Voorhees, P. M., Lopez-Girona, A., Mendy, D., Corral, L. G., Krenitsky, V. P., Xu, W., Moutouh-de Parseval, L., et al. (2008). Targeting the p27 E3 ligase SCF(Skp2) results in p27- and Skp2-mediated cell-cycle arrest and activation of autophagy. Blood 111, 4690-4699.

Cnop, M., Mulder, H., and Igoillo-Esteve, M. (2013). Diabetes in Friedreich ataxia. J Neurochem 126 Suppl 1, 94-102.

Condò, I., Malisan, F., Guccini, I., Serio, D., Rufini, A., and Testi, R. (2010). Molecular control of the cytosolic aconitase/IRP1 switch by extramitochondrial frataxin. Hum Mol Genet 19, 1221-1229.

Condò, I., Ventura, N., Malisan, F., Rufini, A., Tomassini, B., and Testi, R. (2007). In vivo maturation of human frataxin. Hum Mol Genet 16, 1534-1540.

Condò, I., Ventura, N., Malisan, F., Tomassini, B., and Testi, R. (2006). A pool of extramitochondrial frataxin that promotes cell survival. J Biol Chem 281, 16750-16756.

Delatycki, M. B. (2009). Evaluating the progression of Friedreich ataxia and its treatment. J Neurol 256 Suppl 1, 36-41.

Ding, K., Lu, Y., Nikolovska-Coleska, Z., Wang, G., Qiu, S., Shangary, S., Gao, W., Qin, D., Stuckey, J., Krajewski, K., et al. (2006). Structure-based design of spiro-oxindoles as potent, specific small-molecule inhibitors of the MDM2-p53 interaction. Journal of medicinal chemistry 49, 3432-3435.

Glickman, M. H., and Ciechanover, A. (2002). The ubiquitin-proteasome proteolytic pathway: destruction for the sake of construction. Physiological reviews 82, 373-428.

Greene, E., Mahishi, L., Entezam, A., Kumari, D., and Usdin, K. (2007). Repeat-induced epigenetic changes in intron 1 of the frataxin gene and its consequences in Friedreich ataxia. Nucleic Acids Res 35, 3383-3390.

Herman, D., Jenssen, K., Burnett, R., Soragni, E., Perlman, S. L., and Gottesfeld, J. M. (2006). Histone deacetylase inhibitors reverse gene silencing in Friedreich's ataxia. Nat Chem Biol 2, 551-558.

Issaeva, N., Bozko, P., Enge, M., Protopopova, M., Verhoef, L. G., Masucci, M., Pramanik, A., and Selivanova, G. (2004). Small molecule RITA binds to p53, blocks p53-HDM-2 interaction and activates p53 function in tumors. Nature medicine 10, 1321-1328.

Kisselev, A. F., van der Linden, W. A., and Overkleeft, H. S. (2012). Proteasome inhibitors: an expanding army attacking a unique target. Chemistry & biology 19, 99-115.

Koutnikova, H., Campuzano, V., and Koenig, M. (1998). Maturation of wild-type and mutated frataxin by the mitochondrial processing peptidase. Hum Mol Genet 7, 1485-1489.

Kussie, P. H., Gorina, S., Marechal, V., Elenbaas, B., Moreau, J., Levine, A. J., and Pavletich, N. P. (1996). Structure of the MDM2 oncoprotein bound to the p53 tumor suppressor transactivation domain. Science 274, 948-953.

Marmolino, D., Acquaviva, F., Pinelli, M., Monticelli, A., Castaldo, I., Filla, A., and Cocozza, S. (2009). PPAR-gamma agonist Azelaoyl PAF increases frataxin protein and mRNA expression: new implications for the Friedreich's ataxia therapy. Cerebellum 8, 98-103.

Martelli, A., and Puccio, H. (2014). Dysregulation of cellular iron metabolism in Friedreich ataxia: from primary iron-sulfur cluster deficit to mitochondrial iron accumulation. Front Pharmacol 5, 130.

Pandolfo, M. (2009). Friedreich ataxia: the clinical picture. J Neurol 256 *Suppl* 1, 3-8.

Parkinson, M. H., Boesch, S., Nachbauer, W., Mariotti, C., and Giunti, P. (2013). Clinical features of Friedreich's ataxia: classical and atypical phenotypes. J Neurochem 126 *Suppl* 1, 103-117.

Pastore, A., and Puccio, H. (2013). Frataxin: a protein in search for a function. J Neurochem 126 *Suppl* 1, 43-52.

Paupe, V., Dassa, E. P., Goncalves, S., Auchere, F., Lonn, M., Holmgren, A., and Rustin, P. (2009). Impaired nuclear Nrf2 translocation undermines the oxidative stress response in Friedreich ataxia. PLoS One 4, e4253.

Perdomini, M., Belbellaa, B., Monassier, L., Reutenauer, L., Messaddeq, N., Cartier, N., Crystal, R. G., Aubourg, P., and Puccio, H. (2014). Prevention and reversal of severe mitochondrial cardiomyopathy by gene therapy in a mouse model of Friedreich's ataxia. Nature medicine 20, 542-547.

Rentsch, A., Landsberg, D., Brodmann, T., Bulow, L., Girbig, A. K., and Kalesse, M. (2013). Synthesis and pharmacology of proteasome inhibitors. Angewandte Chemie 52, 5450-5488.

Richardson, P. G., Mitsiades, C., Hideshima, T., and Anderson, K. C. (2006). Bortezomib: proteasome inhibition as an effective anticancer therapy. Annu Rev Med 57, 33-47.

Rotig, A., de Lonlay, P., Chretien, D., Foury, F., Koenig, M., Sidi, D., Munnich, A., and Rustin, P. (1997). Aconitase and mitochondrial iron-sulphur protein deficiency in Friedreich ataxia. Nat Genet 17, 215-217.

Roxburgh, P., Hock, A. K., Dickens, M. P., Mezna, M., Fischer, P. M., and Vousden, K. H. (2012). Small molecules that bind the Mdm2 RING stabilize and activate p53. Carcinogenesis 33, 791-798.

Rufini, A., Fortuni, S., Arcuri, G., Condo, I., Serio, D., Incani, O., Malisan, F., Ventura, N., and Testi, R. (2011). Preventing the ubiquitin-proteasome-dependent degradation of frataxin, the protein defective in Friedreich's ataxia. Hum Mol Genet 20, 1253-1261.

Sakamoto, N., Ohshima, K., Montermini, L., Pandolfo, M., and Wells, R. D. (2001). Sticky DNA, a self-associated complex formed at long GAA*TTC repeats in intron 1 of the frataxin gene, inhibits transcription. The Journal of biological chemistry 276, 27171-27177.

Schulz, J. B., Boesch, S., Burk, K., Dun, A., Giunti, P., Mariotti, C., Pousset, F., Schols, L., Vankan, P., and Pandolfo, M. (2009). Diagnosis and treatment of Friedreich ataxia: a European perspective. Nat Rev Neurol 5, 222-234.

Shan, Y., Schoenfeld, R. A., Hayashi, G., Napoli, E., Akiyama, T., Iodi Carstens, M., Carstens, E. E., Pook, M. A., and Cortopassi, G. A. (2013). Frataxin deficiency leads to defects in expression of antioxidants and Nrf2 expression in dorsal root ganglia of the Friedreich's ataxia YG8R mouse model. Antioxid Redox Signal 19, 1481-1493.

Shen, M., Schmitt, S., Buac, D., and Dou, Q. P. (2013). Targeting the ubiquitin-proteasome system for cancer therapy. Expert opinion on therapeutic targets 17, 1091-1108.

Soucy, T. A., Smith, P. G., Milhollen, M. A., Berger, A. J., Gavin, J. M., Adhikari, S., Brownell, J. E., Burke, K. E., Cardin, D. P., Critchley, S., et al. (2009). An inhibitor of NEDD8-activating enzyme as a new approach to treat cancer. Nature 458, 732-736.

Tomassini, B., Arcuri, G., Fortuni, S., Sandi, C., Ezzatizadeh, V., Casali, C., Condo, I., Malisan, F., Al-Mandawi, S., Pook, M., et al. (2012). Interferon gamma upregulates frataxin and corrects the functional deficits in a Friedreich ataxia model. Hum Mol Genet 21, 2855-2861.

Vassilev, L. T., Vu, B. T., Graves, B., Carvajal, D., Podlaski, F., Filipovic, Z., Kong, N., Kammlott, U., Lukacs, C., Klein, C., et al. (2004). In vivo activation of the p53 pathway by small-molecule antagonists of MDM2. Science 303, 844-848.

Vaubel, R. A., and Isaya, G. (2013). Iron-sulfur cluster synthesis, iron homeostasis and oxidative stress in Friedreich ataxia. Mol Cell Neurosci 55, 50-61.

Weidemann, F., Stork, S., Liu, D., Hu, K., Herrmann, S., Ertl, G., and Niemann, M. (2013). Cardiomyopathy of Friedreich ataxia. J Neurochem 126 Suppl 1, 88-93.

Wu, L., Grigoryan, A. V., Li, Y., Hao, B., Pagano, M., and Cardozo, T.J. (2012). Specific small molecule inhibitors of Skp2-mediated p27 degradation. Chemistry & biology 19, 1515-1524.

Yandim, C., Natisvili, T., and Festenstein, R. (2013). Gene regulation and epigenetics in Friedreich's ataxia. J Neurochem 126 Suppl 1, 21-42.

Yang, Y., Ludwig, R. L., Jensen, J. P., Pierre, S. A., Medaglia, M. V., Davydov, I. V., Safiran, Y. J., Oberoi, P., Kenten, J. H., Phillips, A. C., et al. (2005). Small molecule inhibitors of HDM2 ubiquitin ligase activity stabilize and activate p53 in cells. Cancer cell 7, 547-559.

Zhang, W., and Sidhu, S. S. (2014). Development of inhibitors in the ubiquitination cascade. FEBS letters 588, 356-367.

What is claimed is:

1. A method of treating Friedreich's ataxia in a subject in need thereof, comprising administering to a subject a therapeutically effective amount of a polycyclic compound or a pharmaceutically acceptable salt, tautomer, or stereoisomer thereof;

wherein the polycyclic compound is of a formula:

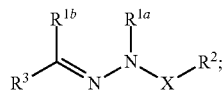

wherein:

X is a linking group selected from the group consisting of —S(O)$_2$— and —C(O)—;

$R^{1a}$ and $R^{1b}$ are each independently selected from the group consisting of hydrogen and $C_1$-$C_6$ alkyl;

$R^2$ is a cyclic group selected from the group consisting of phenyl and naphthyl; wherein the $R^2$ group has from 0 to 3 $R^4$ substituents;

$R^3$ is a phenothiazinyl group with from 0 to 3 $R^4$ substituents; and each $R^4$ substituent is independently selected from the group consisting of $C_1$-$C_6$ alkyl, halo, —NO$_2$, —CF$_3$, —CN, hydroxyl, and $C_1$-$C_6$ alkoxy.

2. The method of claim 1, wherein X is —S(O)$_2$—.

3. The method of claim 1, wherein X is —C(O)—.

4. The method of claim 3, wherein $R^{1b}$ is $C_1$-$C_6$ alkyl.

5. The method of claim 1, wherein $R^2$ is selected from the group consisting of:

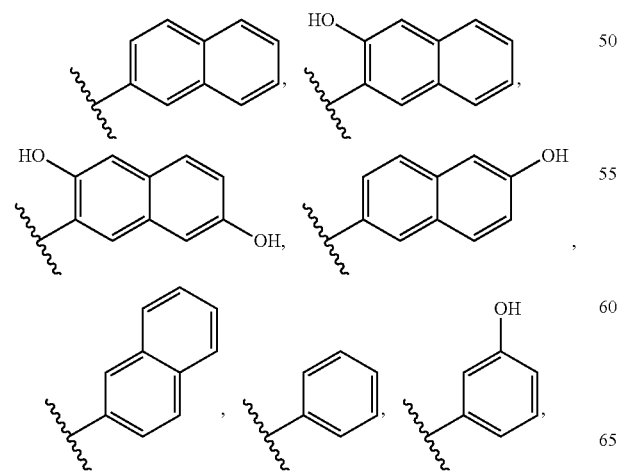

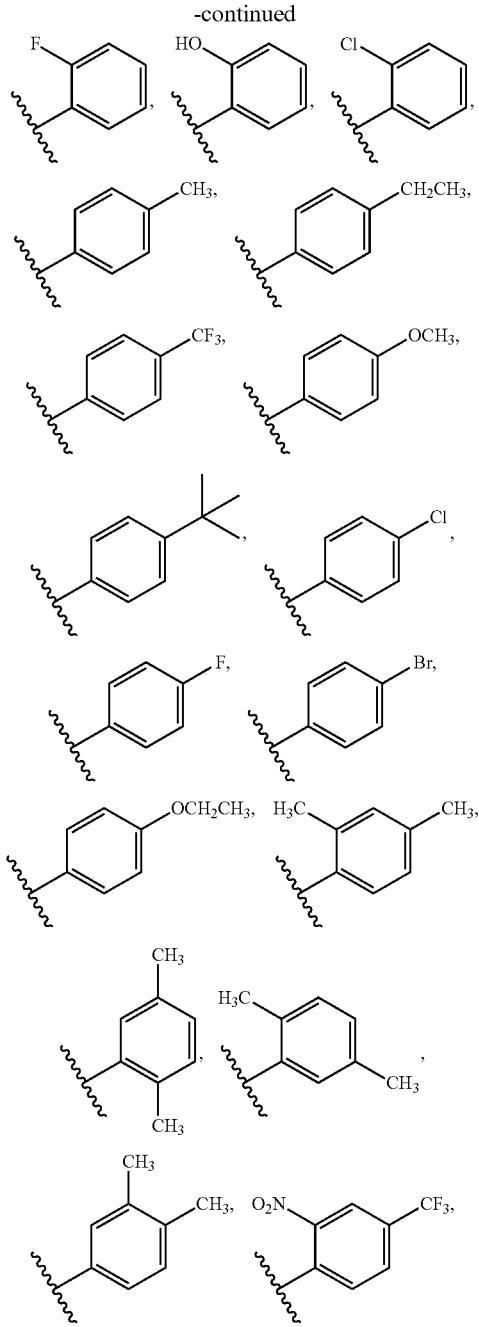

-continued

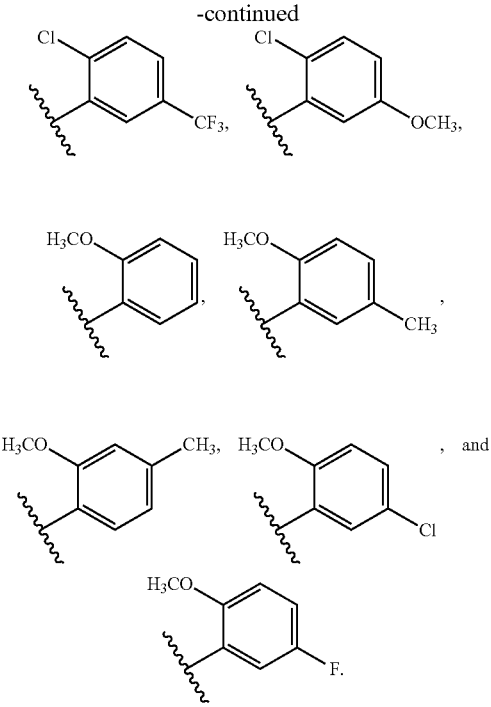

6. The method of claim 1, wherein the $R^4$ substituents for the $R^2$ groups are independently selected from the group consisting of halo, $C_1$-$C_6$ alkyl, hydroxyl, and $C_1$-$C_6$ alkoxy.

7. The method of claim 1, wherein $R^2$ is a naphthyl group substituted with from 0 to 3 $R^4$ substituents.

8. The method of claim 1, wherein $R^3$ is

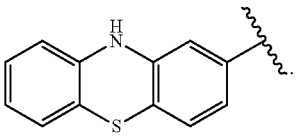 [SMILES: *c1ccc2c(c1)Nc1ccccc1S2]

9. The method of claim 1, wherein $R^{1a}$ or $R^{1b}$ is $C_1$-$C_6$ alkyl;
wherein $R^2$ is phenyl with 0 to 3 $R^4$ substituents; and
wherein the $R^4$ substituents for the $R^3$ groups are independently selected from the group consisting of halo, $C_1$-$C_6$ alkyl, hydroxyl, and $C_1$-$C_6$ alkoxy.

10. The method of claim 9, wherein the compound is of the formula:

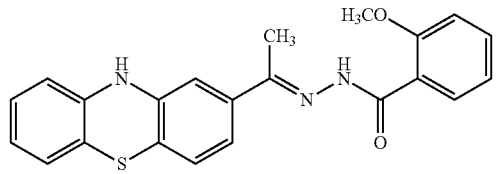

11. The method of claim 1, wherein each $R^4$ is independently $C_1$-$C_6$ alkyl, halo, —$NO_2$, —$CF_3$, —CN, or $C_1$-$C_6$ alkoxy.

12. The method of claim 1, wherein the method of treating Friedreich's ataxia comprises inhibiting ubiquitination of frataxin.

* * * * *

SEQUENCE LISTING

```
<160> NUMBER OF SEQ ID NOS: 1

<210> SEQ ID NO 1
<211> LENGTH: 210
<212> TYPE: PRT
<213> ORGANISM: Homo sapiens

<400> SEQUENCE: 1

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
            20                  25                  30

Leu Ala Pro Leu Cys Gly Arg Arg Gly Leu Arg Thr Asp Ile Asp Ala
        35                  40                  45

Thr Cys Thr Pro Arg Arg Ala Ser Ser Asn Gln Arg Gly Leu Asn Gln
    50                  55                  60

Ile Trp Asn Val Lys Lys Gln Ser Val Tyr Leu Met Asn Leu Arg Lys
65                  70                  75                  80

Ser Gly Thr Leu Gly His Pro Gly Ser Leu Asp Glu Thr Thr Tyr Glu
                85                  90                  95

Arg Leu Ala Glu Glu Thr Leu Asp Ser Leu Ala Glu Phe Phe Glu Asp
            100                 105                 110

Leu Ala Asp Lys Pro Tyr Thr Phe Glu Asp Tyr Asp Val Ser Phe Gly
        115                 120                 125

Ser Gly Val Leu Thr Val Lys Leu Gly Gly Asp Leu Gly Thr Tyr Val
    130                 135                 140
```

```
Ile Asn Lys Gln Thr Pro Asn Lys Gln Ile Trp Leu Ser Ser Pro Ser
145                 150                 155                 160

Ser Gly Pro Lys Arg Tyr Asp Trp Thr Gly Lys Asn Trp Val Tyr Ser
                165                 170                 175

His Asp Gly Val Ser Leu His Glu Leu Leu Ala Ala Glu Leu Thr Lys
            180                 185                 190

Ala Leu Lys Thr Lys Leu Asp Leu Ser Ser Leu Ala Tyr Ser Gly Lys
        195                 200                 205

Asp Ala
210
```